US006565511B2

(12) United States Patent
Panescu et al.

(10) Patent No.: US 6,565,511 B2
(45) Date of Patent: May 20, 2003

(54) SYSTEMS FOR RECORDING USE OF STRUCTURES DEPLOYED IN ASSOCIATION WITH HEART TISSUE

(75) Inventors: Dorin Panescu, Sunnyvale, CA (US); David K. Swanson, Mountain View, CA (US); David F. Dueiri, Mountain View, CA (US); David McGee, Sunnyvale, CA (US); Daniel A. Dupree, Saratoga, CA (US); James G. Whayne, Saratoga, CA (US); Robert R. Burnside, Mountain View, CA (US); Tuan Nguyen, San Jose, CA (US)

(73) Assignee: EP Technologies, Inc., San Jose, CA (US)

(*) Notice: Subject to any disclaimer, the term of this patent is extended or adjusted under 35 U.S.C. 154(b) by 0 days.

(21) Appl. No.: 10/114,779

(22) Filed: Apr. 2, 2002

(65) Prior Publication Data

US 2002/0143250 A1 Oct. 3, 2002

Related U.S. Application Data

(63) Continuation of application No. 09/804,880, filed on Mar. 12, 2001, now Pat. No. 6,490,468, which is a continuation of application No. 09/563,221, filed on May 2, 2000, now Pat. No. 6,221,013, which is a continuation of application No. 08/938,298, filed on Sep. 26, 1997, now Pat. No. 6,086,532.

(51) Int. Cl.[7] .............................................. A61B 8/00
(52) U.S. Cl. ..................................................... 600/437
(58) Field of Search .......................... 600/372, 373–381, 600/386, 393, 395, 407–471, 481–518; 607/99, 101, 113, 122; 606/41, 15, 31; 601/2, 3; 73/625, 626; 367/7, 11, 130, 138; 128/916, 897

(56) References Cited

U.S. PATENT DOCUMENTS

| 4,583,553 A | | 4/1986 | Shah et al. |
| 5,411,025 A | | 5/1995 | Webster, Jr. |
| 5,433,198 A | * | 7/1995 | Desai .......................... 600/374 |
| 5,464,404 A | | 11/1995 | Abela et al. |
| 5,619,991 A | | 4/1997 | Sloane |
| 5,637,090 A | | 6/1997 | McGee et al. |
| 5,666,953 A | | 9/1997 | Wilk |
| 5,681,308 A | | 10/1997 | Edwards et al. |
| 5,743,903 A | | 4/1998 | Stern et al. |
| 5,772,590 A | | 6/1998 | Webster, Jr. |
| 5,782,239 A | | 7/1998 | Webster, Jr. |
| 6,086,532 A | * | 7/2000 | Panescu et al. ............. 600/437 |

FOREIGN PATENT DOCUMENTS

| WO | WO 94/13198 | 6/1994 |
| WO | WO 95/02995 | 2/1995 |
| WO | WO 97/05817 | 2/1997 |

\* cited by examiner

Primary Examiner—Marvin M. Lateef
Assistant Examiner—Ali M. Imam
(74) Attorney, Agent, or Firm—Bingham McCutchen LLP

(57) ABSTRACT

A system records use of a structure deployed in operative association with heart tissue in a patient. An image controller generates an image of the structure while in use in the patient. An input receives data including information identifying the patient. An output processes the image in association with the data as a patient-specific, data base record for storage, retrieval, or manipulation.

14 Claims, 27 Drawing Sheets

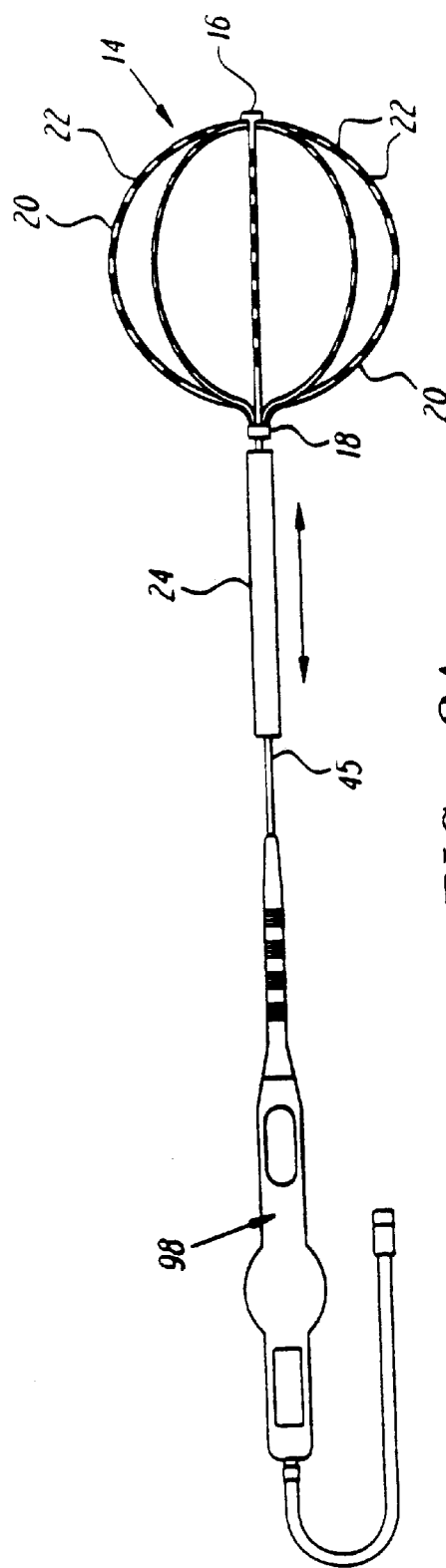
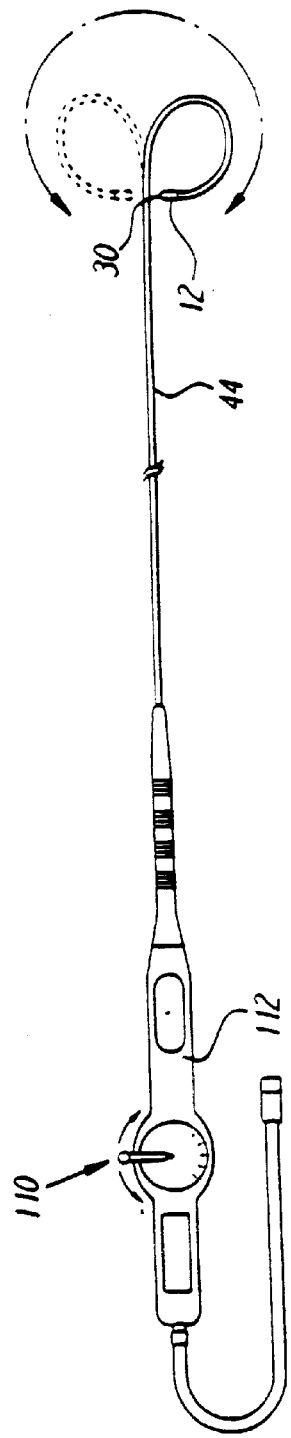
FIG. 2A
FIG. 2B

SYSTEMS FOR RECORDING USE OF STRUCTURES DEPLOYED IN ASSOCIATION WITH HEART TISSUE

RELATED APPLICATION DATA

This application is a continuation of application Ser. No. 09/804,880, filed on Mar. 12, 2001, now U.S. Pat. No. 6,490,468, which is a continuation of application Ser. No. 09/563,221, filed on May 2, 2000, now U.S. Pat. No. 6,221,013, which is a continuation of application Ser. No. 08/938,298, filed on Sep. 26, 1997, now U.S. Pat. No. 6,086,532.

FIELD OF THE INVENTION

The invention generally relates to systems and methods for guiding or locating diagnostic or therapeutic elements in interior regions of the body.

BACKGROUND OF THE INVENTION

Physicians make use of catheters today in medical procedures to gain access into interior regions of the body for diagnostic and therapeutic purposes. It is important for the physician to be able to reliably and precisely position in proximity to desired tissue locations. For example, the need for precise control over the catheter is especially critical during procedures that ablate myocardial tissue from within the heart. These procedures, called ablation therapy, are used to treat cardiac rhythm disturbances.

SUMMARY OF THE INVENTION

One aspect of the invention provides a system to record use of a structure deployed in operative association with heart tissue in a patient. An image controller generates an image of the structure while in use in the patient. An input receives data including information identifying the patient. An output processes the image in association with the data as a patient-specific, data base record for storage, retrieval, or manipulation.

In a preferred embodiment, the data that forms part of the data base record include other relevant information. For example, the data includes information identifying the procedure, or diagnostic information, or therapeutic information, or time stamped information, or processing information documenting the storage, retrieval, or manipulation of the data, or information identifying a person other than the patient (such as the attending physician). In a preferred embodiment, the output password-protects the data base record.

In a preferred embodiment, the image controller includes functions to alter orientation, or shape, or view aspects of the image before or after processing by the output. In a preferred embodiment, the image controller also includes functions to mark or otherwise annotate one or more regions of the image in response to operator input before or after processing by the output.

In a preferred embodiment, the image controller generates a proximity-indicating output showing the proximity of a roving element, deployed in the patient, to the structure.

Another aspect of the invention provides a system for diagnosing or treating cardiac conditions of multiple patients. The system includes a network of local work stations, each one adapted to be coupled to an electrode structure, which, in use, is deployed in operative association with heart tissue of a patient. Each local work station includes an image controller to generate an image of the structure at least partially while the operative element performs a procedure in an interior body region. An input receives data including information identifying the patient, and an output processes the image in association with the data as a patient-specific, data base record for storage, retrieval, or manipulation. The system further includes a central terminal coupled to the output of each work station. The central terminal receives the patient-specific data base records for all work stations for storage in a central patient data base.

Other features and advantages of the inventions are set forth in the following Description and Drawings, as well as in the appended claims.

BRIEF DESCRIPTION OF THE DRAWINGS

FIG. 2A is a side view of the three-dimensional basket structure carried by a catheter tube, which forms a part of the system shown in FIG. 1;

FIG. 2B is a side view of the operative element carried by a catheter tube, which forms a part of the system shown in FIG. 1;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

I. Proximity Sensing Within Three-Dimensional Structures

Figure 1:
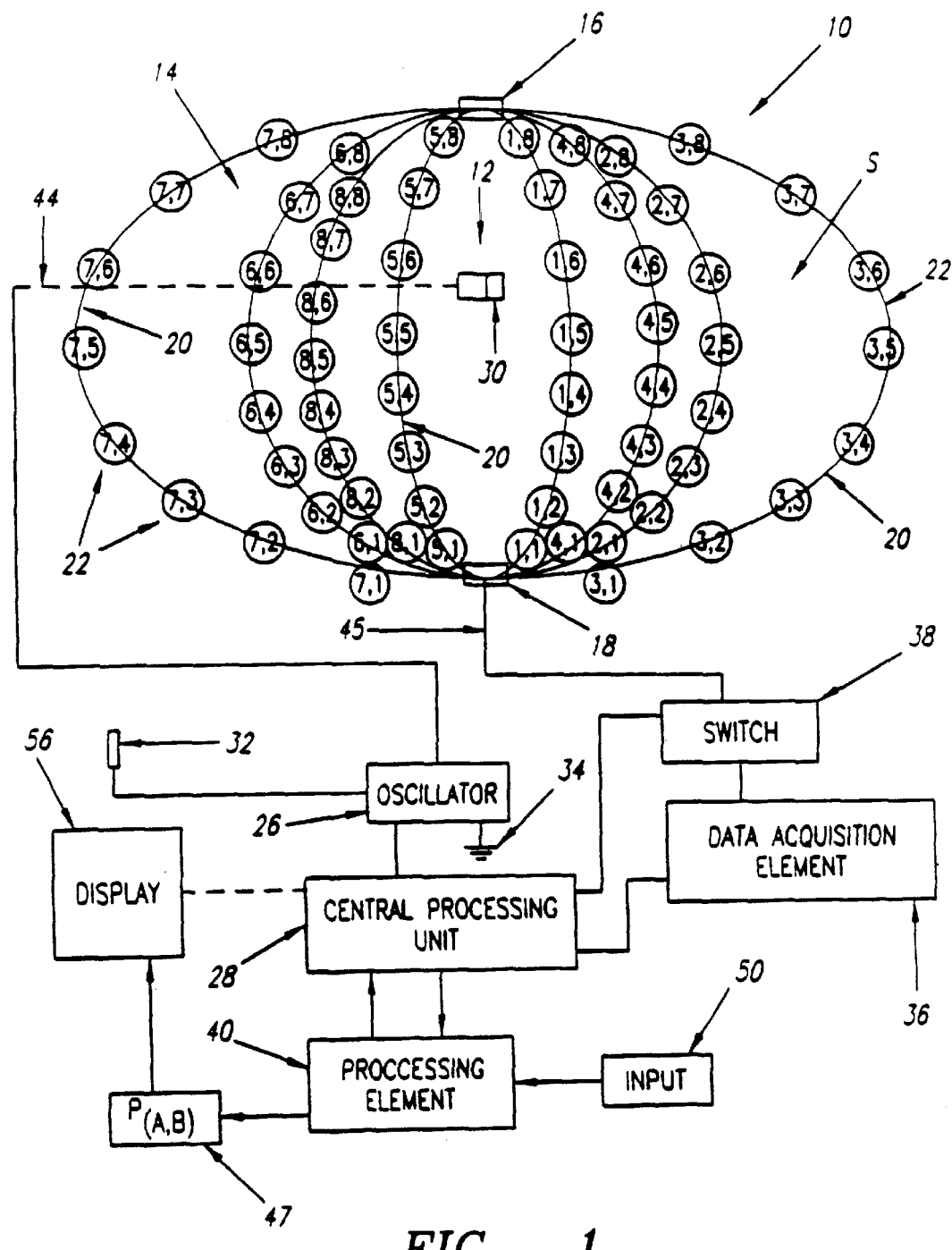
FIG. 1 is schematic view of a system for sensing the position of an operative element within a three-dimensional basket structure, in which an electrode on the operative element transmits an electrical field, which is sensed by one or more electrodes on the basket structure.

FIG. 1 shows one embodiment of a position sensing system 10, which locates the position of an operative element 12 within a space (designated S). The system 10 is well adapted for use inside body lumens, chambers or cavities for either diagnostic or therapeutic purposes. For this reason, the system 10 will be described in the context of its use within a living body. The system 10 particularly lends itself to catheter-based procedures, where access to the interior body region is obtained, for example, through the vascular system or alimentary canal, without complex, invasive surgical procedures.

For example, the system 10 can be used during the diagnosis and treatment of arrhythmia conditions within the heart, such as ventricular tachycardia or atrial fibrillation. The system 10 also can be used during the diagnosis or treatment of intravascular ailments, in association, for example, with angioplasty or atherectomy techniques. The system 10 also can be used during the diagnosis or treatment of ailments in the gastrointestinal tract, the prostrate, brain, gall bladder, uterus, and other regions of the body.

A. The operative Element

For deployment into an interior body space S, the operative element 12 is carried at the distal end of a catheter tube 44 (as FIG. 2B also shows). Nevertheless, the system 10 can also be used in association with systems and methods that are not necessarily catheter-based, e.g., laser delivery devices, atherectomy devices, transmyocardial revascularization (TMR), or percutaneous myocardial revascularization (PMR).

The operative element 12 can take different forms and can be used for either therapeutic purposes, or diagnostic purposes, or both. The operative element 12 can comprise, for example, a device for imaging body tissue, such as an ultrasound transducer or an array of ultrasound transducers, or an optic fiber element. Alternatively, the operative element 12 can comprise a device to deliver a drug or therapeutic material to body tissue. Still alternatively, the operative element 12 can comprise a device, e.g., an electrode, for sensing a physiological characteristic in tissue, such as electrical activity in heart tissue, or for transmitting energy to stimulate or ablate tissue.

B. Three-Dimensional Locating Probe

The system 10 includes a locating probe (see FIG. 2A also), which, like the operative element 12, is carried at the distal end of a catheter tube 45 for introduction into the body space S. In the embodiment illustrated in FIG. 1, the locating probe comprises a composite, three-dimensional basket structure 14. As will be described later, the structure of the locating probe can take other forms.

As best shown in FIG. 2A, the structure 14 includes eight spaced apart spline elements 20 assembled together by a distal hub 16 and a proximal base 18. Each spline 20, in turn, carries eight electrodes 22, for a total of sixty-four electrodes 22 positioned about the space S. Of course, a greater or lesser number of spline elements 20 and/or electrodes 22 can be present.

Each spline element 20 preferably comprises a flexible body made from resilient, inert wire or plastic. Elastic memory material such as nickel titanium (commercially available as NITINOL™ material) can be used. Resilient injection molded plastic or stainless steel can also be used. Each spline element 20 is preferably preformed with a convex bias, creating a normally open three-dimensional basket structure.

As FIG. 2A shows, an outer sheath 24 can be advanced by sliding forward along the catheter tube 45 to compress and collapses the structure 14 for introduction into the body region. Rearward movement retracts the slidable sheath 24 away from the structure 14, which springs open and assumes its three-dimensional shape.

In FIGS. 1 and 2A, the geometry of spline elements 20 is shown to be both radially and axially symmetric. Asymmetric structures, either radially or axially or both, can also be used. Examples of asymmetric arrays of spline structures are shown in copending U.S. application Ser. No. 08/742,569, filed Oct. 28, 1996 and entitled "Asymmetric Multiple Electrode Support Structures," now U.S. Pat. No. 6,216,043, which is incorporated herein by reference.

FIG. 1 identifies the electrodes 22 by the set designation (A,B), where A=1 to p and B=1 to e, where p is the total number of splines 20 and e is the number of electrodes 22 on each spline 20 (in the illustrated embodiment, p=8 and e=8).

It should be appreciated that the locating probe need not be a composite basket structure 14, but instead exist as separate probes located about the space S. However, the composite basket structure 14 is well suited for use within the heart and can perform other functions in addition to navigation, such as pacing and mapping, as will be described in greater detail later.

C. Generation of Proximity-Indicating Output (i) Transmission of Electrical Field by Roving Electrode As FIG. 1 shows, a central processing unit 28 conditions an oscillator 26 to generate an electrical alternating current (AC) waveform at a predetermined amplitude and frequency. The central processing unit 28 couples the oscillator 26 to a transmitting electrode 30 carried by the roving operative element 12. The electrode 30 may be a component added to the operative element 12, or it may comprise a component already on the operative element 12, but used for an additional purpose.

An indifferent electrode 32, carried as a patch on the exterior of the patient, comprises the voltage return, which is, in turn, coupled to an electrical reference. In the illustrated embodiment, the electrical reference is isolated or patient ground 34, although other references can be used. Alternatively, another electrode carried by the operative element 12 can serve as the voltage return. As another alternative, an electrode (A,B) on the structure 14 can also serve as the voltage return. A voltage field is established, which varies in detected amplitude at each basket electrode (A,B) according to its distance from the electrode 30 carried by the operative element 12. For use within a living body space, the selected current amplitude of the oscillator output can vary between 0.1 mAmp to about 5 mAmp. The frequency selected can also vary from about 5 kHz to about 100 kHz. Currents substantially above about 5 mAmp and frequencies substantially below 5 kHz should be avoided when heart tissue is nearby, as they pose the danger of inducing fibrillation. The maximum current that can be used while avoiding fibrillation is a function of the frequency, as expressed in the following equation:

$$I = f \times 10$$

where I is current in $\mu$Amp, and f is frequency in kHz.

The shape of the waveform can also vary. In the illustrated and preferred embodiment, the waveform is sinusoidal. However, square wave shapes or pulses can also be used, although harmonics may be encountered if capacitive coupling is present. Furthermore, the waveform need not be continuous. The oscillator 26 may generate pulsed waveforms.

The system 10 includes a data acquisition element 36 coupled to the central processing unit 28 and to a switch or suitable multiplexer element 38. The switch element 38 individually conditions each electrode (A,B) on the structure 14 to sense a local voltage amplitude $V_{S(A,B)}$. The data acquisition element 36 includes an amplitude detector 37 (see FIG. 3), which acquires $V_{S(A,B)}$ for each electrode 22 in association with the electrode's (A,B) position coordinates.

The switch element 38 also conditions the electrode 30 on the operative element 12 to sense a local voltage amplitude $V_{O(A,B)}$ at the same time $V_{S(A,B)}$ is sensed by each basket electrode (A,B). The data acquisition element 36 includes a second amplitude detector 39 (see FIG. 3), which acquires a $V_{O(A,B)}$ in association with each $V_{S(A,B)}$.

As FIG. 1 further shows, the central processing unit 28 includes a processing element 40. The processing element 40 includes a component 42 (see FIG. 3), which derives a normalized detected voltage value $V_{N(A,B)}$ for each acquired $V_{O(A,B)}$ and $V_{S(A,B)}$ data set, as follows:

$$V_{N(A,B)} = \frac{V_{S(A,B)}}{V_{O(A,B)}}$$

Figure 3:
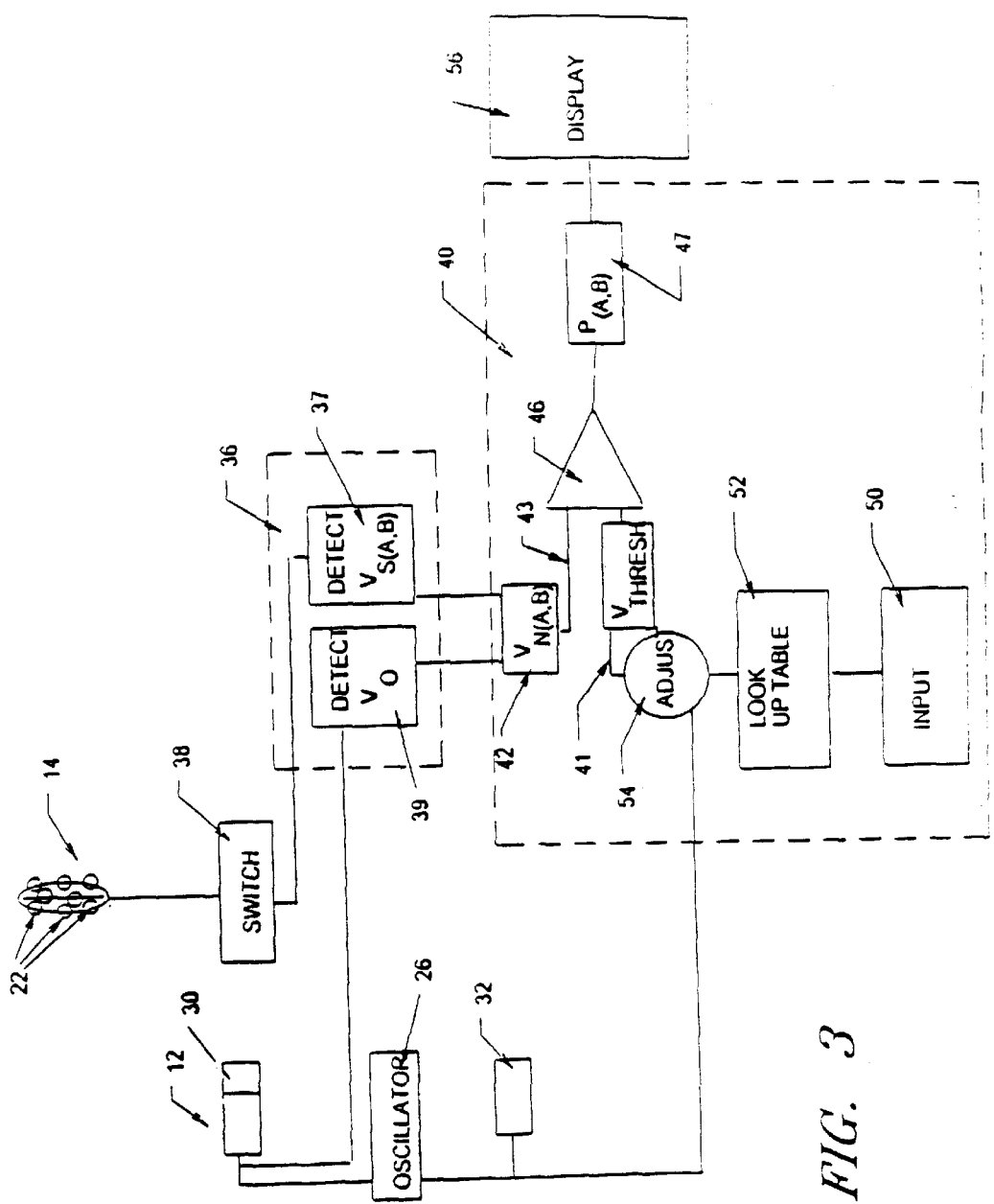
FIG. 3 is a schematic view of the processing element which forms a part of the system shown in FIG. 1.

As FIG. 3 also shows, the processing element 40 further includes a comparator 46. The comparator 46 receives as input 43 the normalized detected voltage value $V_{N(A,B)}$ generated by the component 42. The comparator 46 also receives as input 41 a set line voltage, which constitutes a predetermined nominal voltage threshold value $V_{THRESH}$. The comparator 46 compares the magnitude of $V_{N(A,B)}$ (input line 43) to the magnitude of $V_{THRESH}$ (input line 41).

The predetermined nominal voltage threshold value $V_{THRESH}$ establishes a nominal separation distance between the electrode 30 on the operative element 12 and a given basket electrode (A,B). The threshold voltage value $V_{THRESH}$ serves to differentiate between a "close condition" between the electrode 30 on the operative element 12 and a given basket electrode (A,B) (i.e., equal to or less than the nominal distance) and a "far condition" between the electrode 30 on the operative element 12 and a given basket electrode (A,B) (i.e., greater than the nominal distance).

If $V_{N(A,B)}$ is greater than or equal to $V_{THRESH}$, the comparator 46 generates a proximity-indicating output 47, also designed $P_{(A,B)}$, for the basket electrode (A,B). The proximity-indicated output $P_{(A,B)}$ for a given electrode (A,B) notifies the physician that the requisite "close condition" exists between the electrode 30 on the operative element 12 and the particular basket electrode (A,B).

When $V_{N(A<B)}$ is less than $V_{THRESH}$, the comparator 46 generates no output for the particular electrode (A,B). The absence of a proximity-indicating output $P_{(A,B)}$ for a particular electrode (A,B) notifies the physician that the requisite "far condition" exists between the electrode 30 on the operative element 12 and the particular basket electrode (A,B).

The magnitude selected for the threshold value $V_{THRESH}$ sets the spacial criteria for "close condition" and "far condition," given the physical characteristics of the electrode 30 on the operative element 12 and the physical characteristics of the electrode (A,B) on the structure 14. The physical characteristics include the diameter and shape of the electrode, as well as the electrical conductivity of the material from which the electrode is made and the electrical properties of the conductive medium exiting between the electrode 30 and the structure 14 (for example, a blood pool or myocardial tissue mass)

Figure 4:
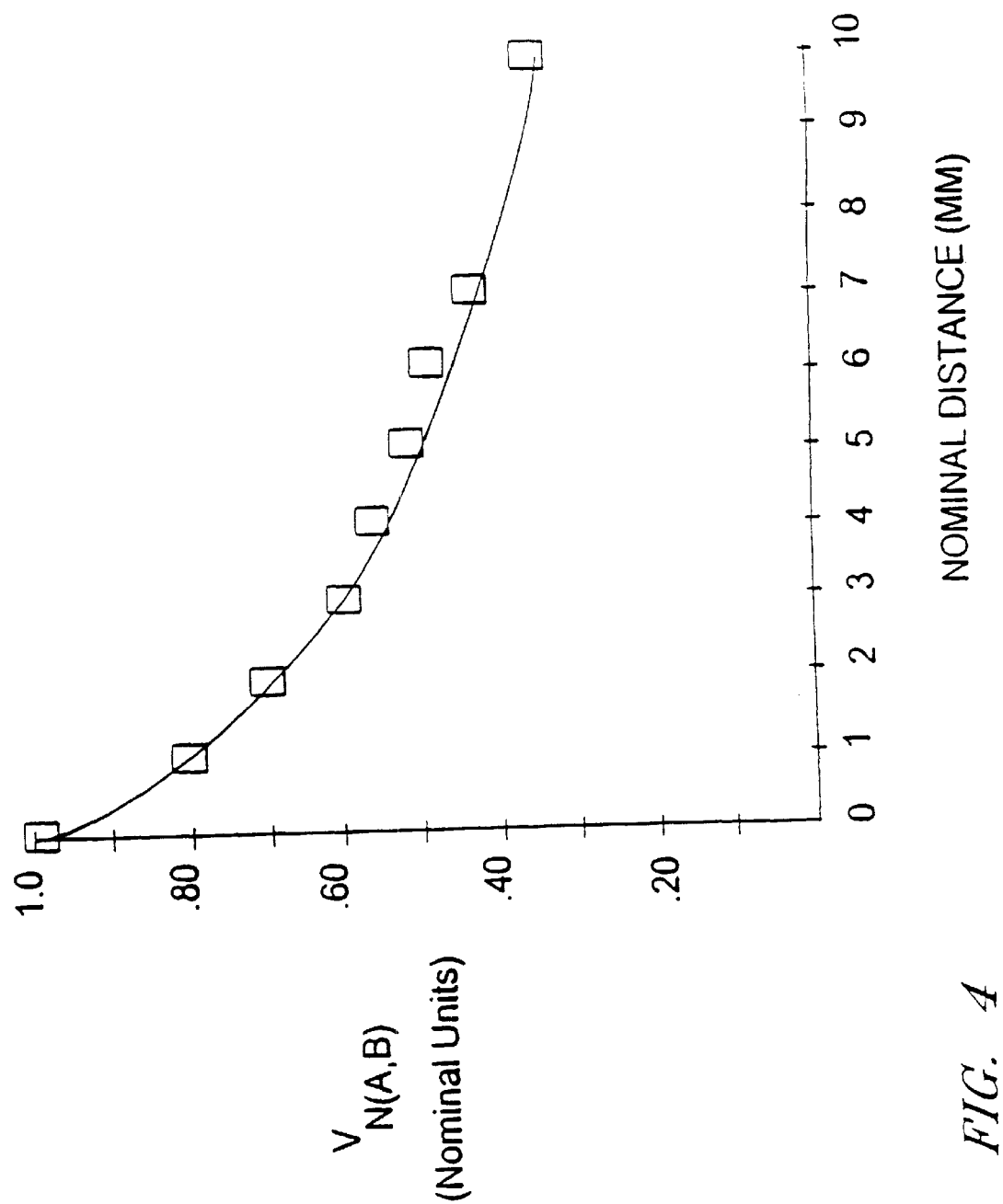
FIG. 4 is a graph exemplifying how normalized voltage sensed by an electrode carried by the three-dimensional basket structure changes in relation to the proximity of the electrode to the operative element, which is a relationship that the system shown in FIG. 1 uses to generate a proximity-indicating output.

The relationship between distance and expected normalized voltage detected value $V_{N(A,B)}$ for a given electrode 30 on the operative element 12 and a given electrode (A,B) on the structure 14 can be determined empirically, e.g., by in vitro or in vivo testing or by finite element analysis. FIG. 4 shows a representative data plot, showing the relationship between expected normalized voltage detected values $V_{N(A,B)}$ for a given electrode type on the operative element 12 and a given electrode type on the structure 14. The plot in FIG. 4 shows that $V_{N(A,B)}$ (which is not expressed in units of volts, as it represents a normalized value derived by dividing two voltages) increases as the distance (in mm) between the electrode 30 and a basket electrode (A,B) decreases. For example, in FIG. 4, at a distance of 4 mm, the expected normalized voltage detected value $V_{N(A,B)}$ is about 0.5 units, whereas, at a distance of about 1 mm, the expected normalized voltage detected value $V_{N(A,B)}$ is about 0.8 units.

By selecting an expected normalized voltage detected value $V_{N(A,B)}$ as the threshold $V_{THRESH}$, the operator is able to define the nominal distance between a given electrode 30 on the operative element 12 and a given electrode (A,B) on the structure 14 at which the proximity-indicating output $P_{(A,B)}$ is first generated.

The threshold value $V_{THRESH}$ is the voltage line input to the comparator 46. The value of $V_{THRESH}$ can be set at a desired fixed voltage value representing a nominal threshold distance. In the illustrated and preferred embodiment, the processing element 40 includes an input 50 by which the physician can designate a value for the nominal distance. For example, the physician can designate the nominal distance within a range of distances of 1 mm to 5 mm. The processing element 40 includes a look-up table 52 or its equivalent, which expresses the empirically determined relationship between voltage and distance (which FIG. 4 exemplifies). Using the table, the processing element 40 converts the distance value entered by input 50 to a corresponding normalized voltage value, which constitutes $V_{THRESH}$. The processing element 40 also includes a voltage regulator 54, which sets the voltage line input to the normalized voltage value ($V_{THRESH}$), to thereby achieve the spatial sensitivity established by the physician for the proximity-indicating output P(A,B).

The operative components controlled by the central processing unit 28, as previously discussed, can incorporate the particular electrical configuration shown in FIGS. 1 and 3, or another analog or digital configuration, to carry out the signal sampling and processing functions as described.

(ii) Transmission of Electrical Field by One or More Stationary Electrodes

Figure 20:
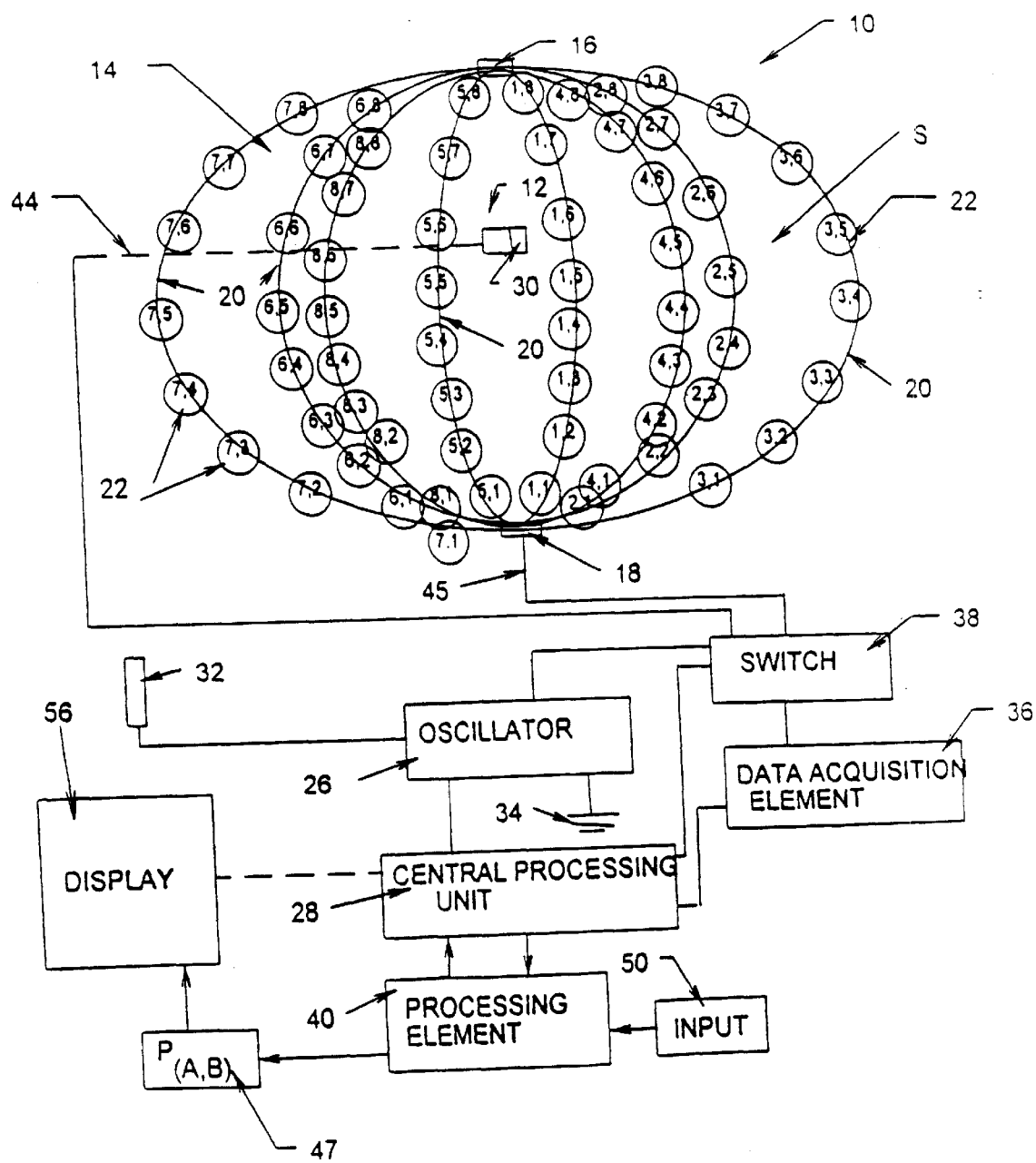
FIG. 20 is schematic view of a system for sensing the position of an operative element within a three-dimensional basket structure, in which one or more electrodes on the basket structure transmit an electrical field, which is sensed by an electrode on the operative element.

As FIG. 20 shows, the central processing unit 28 can couple the oscillator 26 (through the switch or suitable multiplexer element 38) to one or more electrodes 22 carried by the structure 14. The indifferent electrode 32 remains the voltage return, being coupled to an electrical reference, which, in the illustrated embodiment, is isolated or patient ground 34. As before stated, alternatively, another electrode carried by the operative element 12 can serve as the voltage return, or an electrode 22 on the structure 14 can also serve as the voltage return.

The transmission of electrical energy from one or more of the electrodes 22 on the structure 14 to the indifferent electrode 32 establishes a voltage field, like that earlier described in connection with FIGS. 1 and 3. The voltage field will vary in detected amplitude at the roving electrode 30 according to its distance from the transmitting basket electrode (A,B).

In this configuration (see FIG. 21, as well) the switch element 38 individually conditions a selected one or group of electrodes (A,B) on the structure 14 to transmit electrical energy. The switch element 38 also conditions each selected transmitting electrode (A,B) on the structure 14 to sense a local voltage amplitude $V_{S(A,B)}$. The data acquisition element 36 includes the amplitude detector 37 (see FIG. 21), which acquires $V_{S(A,B)}$ for each transmitting electrode 22 in association with the electrode's (A,B) position coordinates.

The switch element 36 also conditions the electrode 30 on the operative element 12 to sense a local voltage amplitude $V_{O(A,B)}$ at the same time $V_{S(A,B)}$ is sensed by each transmitting basket electrode (A,B). The data acquisition element 36 includes the second amplitude detector 39 (see FIG. 21), which acquires a $V_{O(A,B)}$ in association with each $V_{S(A,B)}$.

The component 42 of the processing element 40 (see FIG. 21) derives a normalized detected voltage value $V_{N(A,B)}$ for each acquired $V_{O(A,B)}$ and $V_{S(A,B)}$ data set, as follows:

$$V_{N(A,B)} = \frac{V_{O(A,B)}}{V_{S(A,B)}}$$

Figure 21:
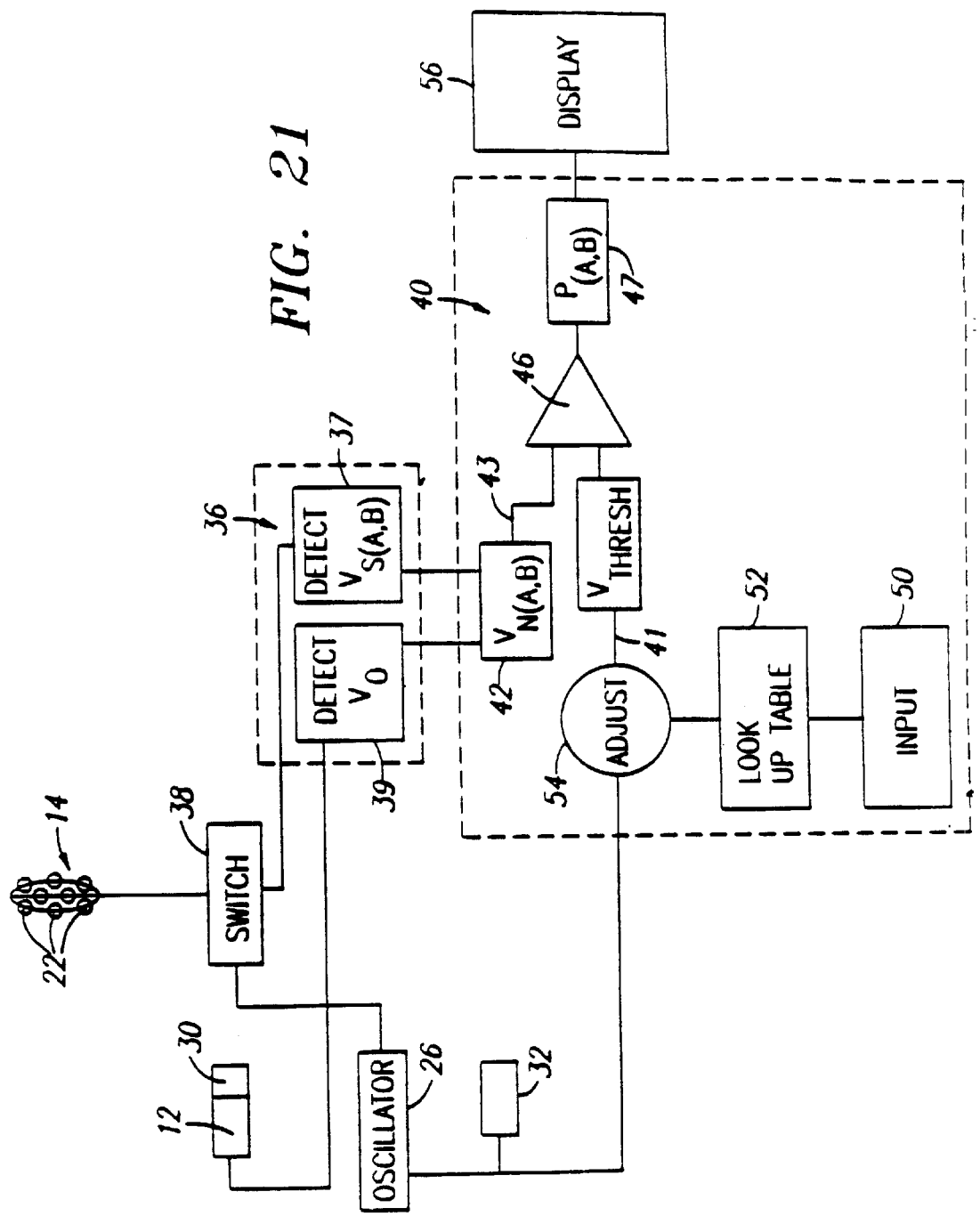
FIG. 21 is a schematic view of the processing element which forms a part of the system shown in FIG. 20.

Although the positions of the numerator and denominator quantities are reversed for $V_{N(A,B)}$ in the embodiment shown in FIGS. 20 and 21, compared to the embodiment shown in FIGS. 1 and 3, the normalized detected voltage value $V_{N(A,B)}$ is derived in the same conceptual way. More universally expressed, the normalized detected voltage value $V_{N(A,B)}$ is derived by dividing the local voltage amplitude sensed by the transmitting electrode $V_{TRANS}$ into the local voltage amplitude sensed by the other non-transmitting, sense-only electrode $V_{SENSE}$, or:

$$V_N = \frac{V_{SENSE}}{V_{TRANS}}$$

As FIG. 21 shows, the processing element 40 includes the comparator 46. The comparator 46 receives as input 43 the normalized detected voltage value $V_{N(A,B)}$ generated by the component 42. The comparator 46 also receives as input 41 a set line voltage, which constitutes the predetermined nominal voltage threshold value $V_{THRESH}$, as previously described. The comparator 46 compares the magnitude of $V_{N(A,B)}$ (input line 43) to the magnitude of $V_{THRESH}$ (input line 41). Also as previously described, if $V_{N(A,B)}$ is greater than or equal to $V_{THRESH}$, the comparator 46 generates a proximity-indicating output 47 (also designed $P_{(A,B)}$) for the basket electrode (A,B). Conversely, when $V_{N(A,B)}$ is less than $V_{THRESH}$, the comparator 46 generates no output for the particular electrode (A,B).

Figure 22:
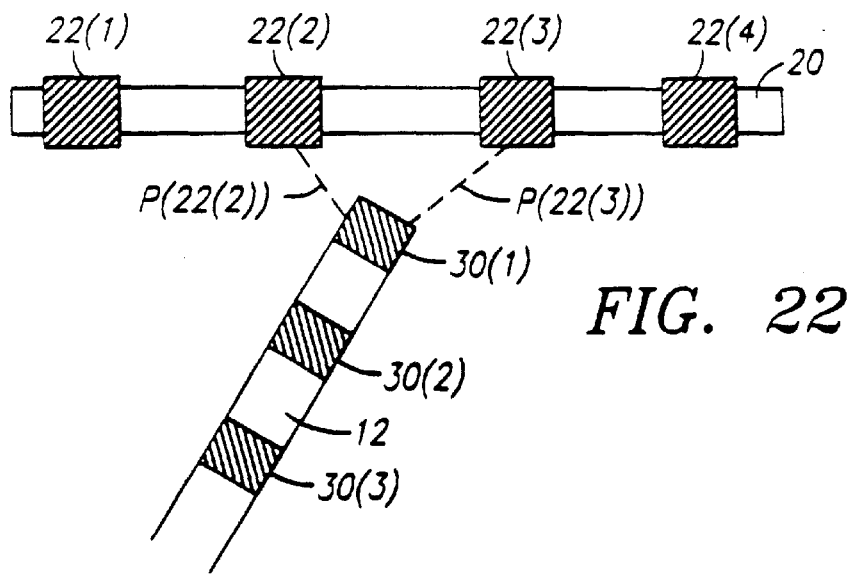
FIG. 22 is schematic view of an operative element oriented with a spline of the basket structure, as shown in FIG. 20, in which the electrical field is sensed by multiple electrodes on the operative element, which is shown in a not-parallel orientation with respect to the spline.

As FIG. 22 shows, the roving element 12 can carry several sensing electrodes (three are shown for purposes of illustration, designated 30(1), 30(2), and 30(1)). The use of several sensing electrodes 30(1), 30(2), and 30(3) in the embodiment shown in FIGS. 20 and 22 allows the physician to assess, not only proximity information, but also information pertaining to the orientation of the roving element 12 itself.

More particularly, the switch element 38 individually conditions all electrodes (A,B) along an entire spline 20 of the structure 14 to transmit electrical energy and to sense a local voltage amplitude $V_{S(A,B)}$ at each transmitting electrode (A,B) along the spline 20. The switch element 38 also conditions each electrode 30(1), 30(2), and 30(3) on the operative element 12 to sense a local voltage amplitude $V_{O(A,B)}$ at the same time $V_{S(A,B)}$ is sensed by each transmitting basket electrode (A,B). The normalized detected voltage value $V_{N(A,B)}$ is generated for each combination of transmitting basket electrode (A,B) and non-transmitting, sense-only electrode 30(1), 30(2), and 30(3) and compared the magnitude of the threshold voltage $V_{THRESH}$ (input line 41).

The resulting generation of one or more proximity-indication outputs provides orientation information. For example, in FIG. 22, the axis of the roving element 12 is oriented in a not-parallel relationship with axis of the spline 20. The roving electrode 30(1) lays in a close condition to only two of the spline electrodes 22(2) and 22(3). The resulting two proximity-indicating outputs P(22(2)) and P(22(3)) for the electrode 30(1), and the absence of proximity-indicating outputs for the other roving electrodes 30(2) and 30(3), denotes that the axis of the roving element 12 is oriented generally not-parallel or "head-on" with respect to the axis of the spline 20.

Figure 23:
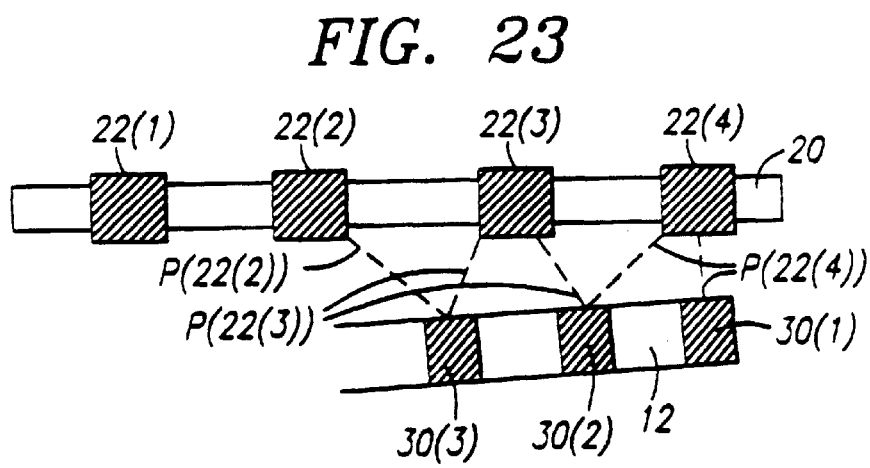
FIG. 23 is schematic view of the operative element oriented with the spline, like that shown in FIG. 22, except that the operative element is shown in more-parallel orientation with respect to the spline.

In FIG. 23, the axis of the roving element 12 is oriented in a more-parallel relationship with the spline 20. In this orientation, the roving electrode 30(1) lays in a close condition to the spline electrode 22(4); the roving electrode 30(2) lays in a close condition to two spline electrodes 22(3) and 22(4); and the roving electrode 30(3) lays in a close condition to two spline electrodes 22(2) and 22(3). Multiple proximity-indicating outputs result: one output P(22(4)) for roving electrode 30(1); two outputs P(22(4)) and P(22(3)) for roving electrode 30(2); and two outputs P(22(2)) and P(22(3)) for roving electrode 30(3). The pattern of proximity-indicating outputs for all roving electrodes 30(1), 30(2), and 30(3) denotes that the roving element 12 is oriented generally parallel or "side-by-side" with respect to the axis of the spline 20.

Transmitting an electrical field from all electrodes along a spline, sequentially about each spline of a three-dimensional basket structure 14, generates a pattern of proximity-indicating outputs. The pattern locates the position and orientation of the operative element 12 within the three-dimensional space the basket structure 14 defines.

More particularly, as FIGS. 22 and 23 demonstrate, for a given electrode 30(1), 30(2), or 30(3) selected on the roving element 12, the number proximity-indicating outputs varies according to proximity of the selected electrode to one or more the electrodes 22(1), 22(2), 22(3), and 22(4) on the spline 20. The number of proximity-indicating outputs for a given electrode 30(1), or 30(2), or 30(3) will increase in proportion to the number of basket electrodes 22(1) to 22(4) in proximity to it. As FIGS. 22 and 23 also demonstrate, the total number of position-indicating outputs combined for all the electrodes 30(1) to 30(3) varies according to the orientation of the axis of the roving electrode to the axis of the spline 20. As the axis of the roving electrode 12 becomes more parallel to the axis of the spline 20, the total number of proximity-indicated outputs for all the electrodes 30(1) to 30(3) will increase.

As will be described in greater detail later, the pattern of multiple, simultaneous proximity-indicating outputs can be interpolated for display purposes.

(iii) Transmission of Electrical Field by an Other Roving Electrode

Figure 29:
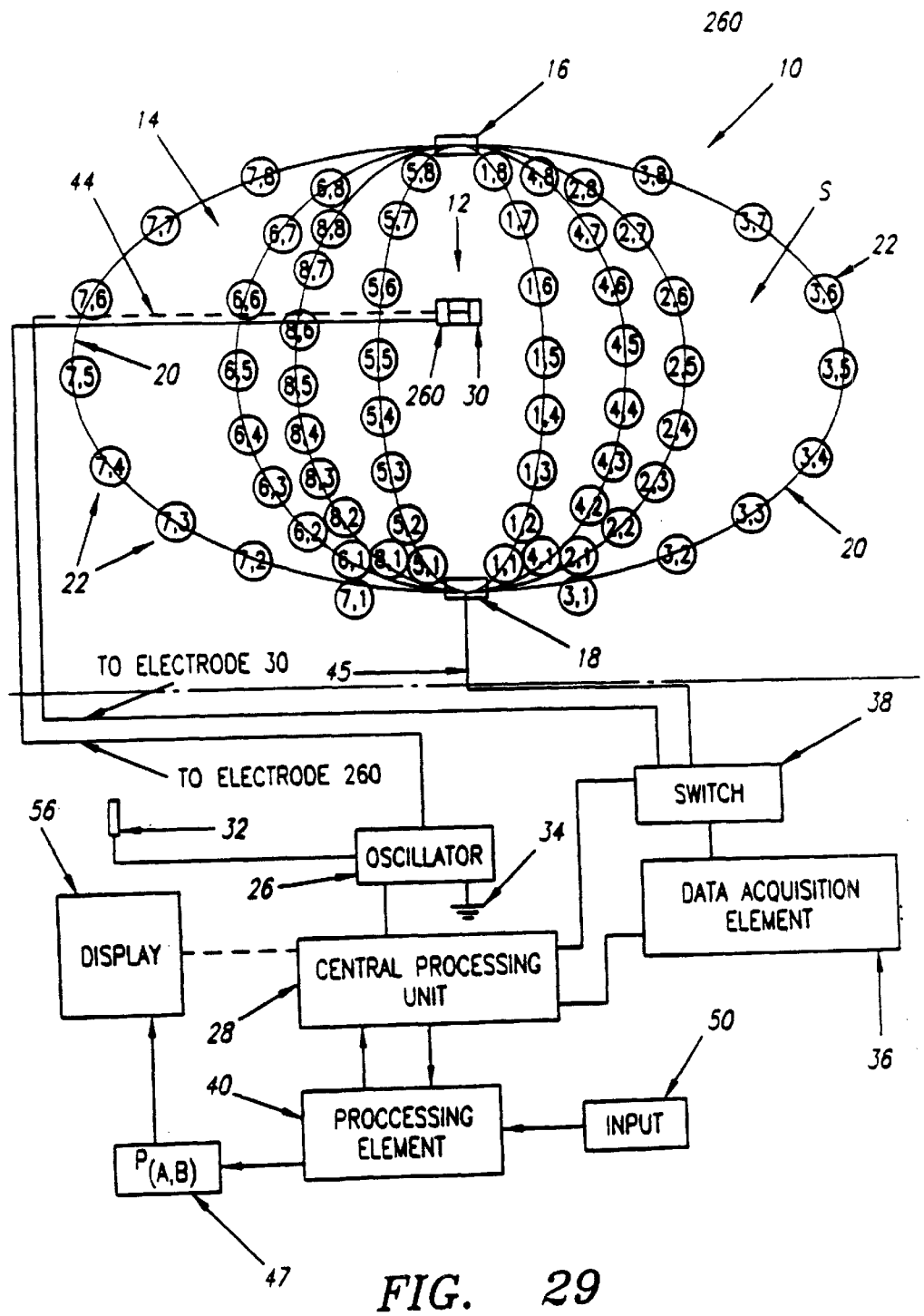
FIG. 29 is schematic view of a system for sensing the position of an operative element within a three-dimensional basket structure, in which one electrode on the operative element transmits an electrical field, which is sensed by an other electrode on the operative element and by one or more electrodes on the basket structure.

As FIG. 29 shows, the roving operative element 12 can carry, in addition to a single sensing electrode 30 or multiple sensing electrodes 30(1), 30(2), and 30(3), an energy transmitting electrode 260. In the illustrated embodiment, the electrode 260 comprises a ring of electrically conductive material, spaced proximally of the single or multiple sensing electrodes 30. Of course, the electrode 260 can take other forms, as will be discussed later in connection with other electrode structures.

In this embodiment, the central processing unit 28 couples the oscillator 26 to the roving electrode 260. The indifferent electrode 32 remains the voltage return, being coupled to an electrical reference, which, in the illustrated embodiment, is isolated or patient ground 34. As before stated, alternatively, another electrode carried by the operative element 12 can serve as the voltage return, or an electrode 22 on the structure 14 can also serve as the voltage return.

The transmission of electrical energy from the electrode 260 to the indifferent electrode 32 establishes a voltage field, like that earlier described in connection with FIGS. 1 and 3, and FIGS. 20 and 21. The voltage field will vary in detected amplitude at the roving electrode 30 according to its distance from a given electrode (A,B) on the structure 14.

In this embodiment, neither the roving electrode 30 nor any of the electrodes (A,B) on the structure 14 transmits the electrical field. Instead (see FIG. 30) the switch element 38 individually conditions a selected one or group of electrodes (A,B) on the structure 14 to sense a local voltage amplitude $V_{S(A,B)}$. The data acquisition element 36 includes the amplitude detector 37 (see FIG. 30), which acquires $V_{S(A,B)}$ for each electrode 22 in association with the electrode's (A,B) position coordinates.

The switch element 36 also conditions the sensing electrode or electrodes 30 on the operative element 12 to sense a local voltage amplitude $V_{O(A,B)}$ at the same time $V_{S(A,B)}$ is sensed by each transmitting basket electrode (A,B). The data acquisition element 36 includes the second amplitude detector 39 (see FIG. 30), which acquires a $V_{O(A,B)}$ in association with each $V_{S(A,B)}$.

The component 42 of the processing element 40 (see FIG. 30) derives a normalized detected voltage value $V_{N(A,B)}$ for each acquired $V_{O(A,B)}$ and $V_{S(A,B)}$ data set, as follows:

$$V_{N(A,B)} = \frac{V_{S(A,B)}}{V_{O(A,B)}}$$

Figure 30:
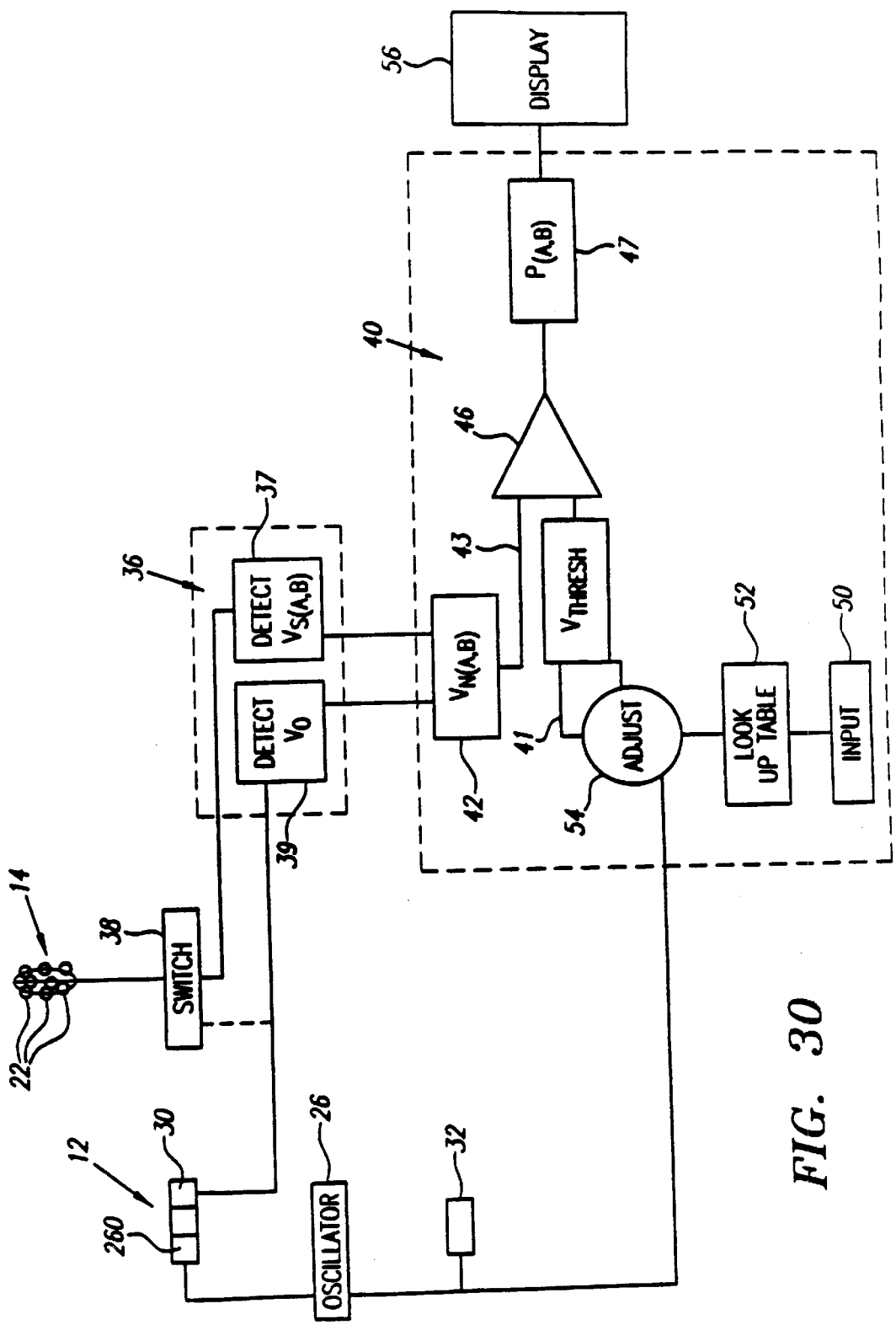
FIG. 30 is a schematic view of the processing element which forms a part of the system shown in FIG. 29.

As FIG. 30 shows, the processing element 40 includes the comparator 46. The comparator 46 receives as input 43 the normalized detected voltage value $V_{N(A,B)}$ generated by the component 42. The comparator 46 also receives as input 41 a set line voltage, which constitutes the predetermined nominal voltage threshold value $V_{THRESH}$, as previously described. The comparator 46 compares the magnitude of $V_{N(A,B)}$ (input line 43) to the magnitude of $V_{THRESH}$ (input line 41). Also as previously described, if $V_{N(A,B)}$ is greater than or equal to $V_{THRESH}$, the comparator 46 generates a proximity-indicating output 47 (also designed $P_{(A,B)}$) for the basket electrode (A,B). Conversely, when $V_{N(A,B)}$ is less than $V_{THRESH}$, the comparator 46 generates no output for the particular electrode (A,B).

D. Displaying the Proximity-Indicating Output

In the illustrated and preferred embodiment, the system 10 includes an output display device 56 coupled to the processing element 40. The device 56 presents the presence or absence of proximity-indicating outputs $P_{(A,B)}$ for each basket electrode (A,B) in a visual or graphic format useful to the physician for remotely locating and guiding the operative element 12 relative to the structure 14.

(i) Hard-Wired Polar Grid

Figure 5:
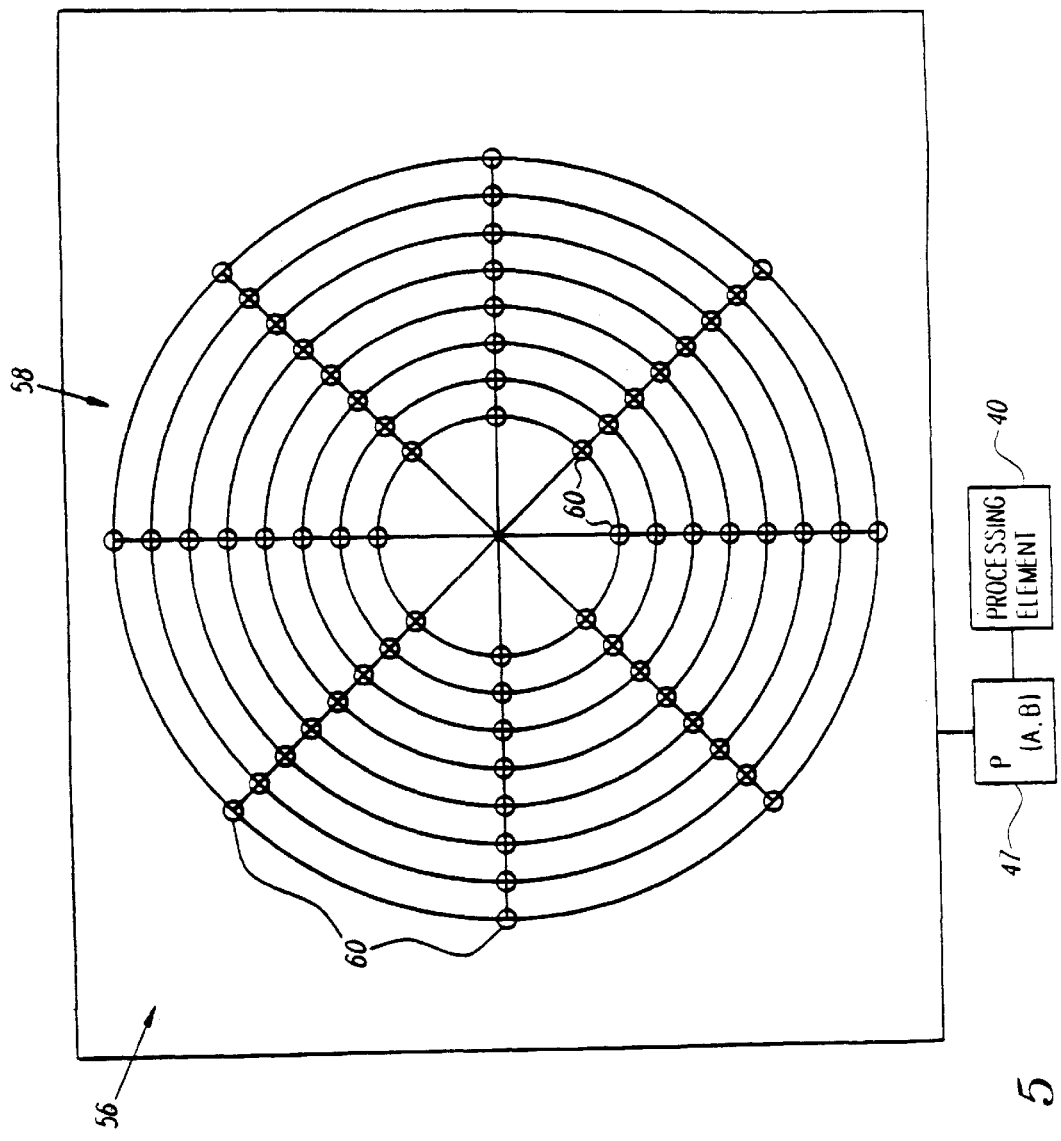
FIG. 5 is a hard-wired display device displaying a polar view of a three-dimensional basket structure, which visually displays the presence or absence of a proximity-indicated output at each electrode carried by the three-dimensional basket structure.

In one embodiment (see FIG. 5), the output display device 56 comprises a hard-wired grid 58 of individual light emitting diodes 60 (LED's) arranged to depict a polar map of all the electrodes (A,B) carried by the basket structure 14. The LED's 60 are normally maintained in an designated "OFF" state by the processing element 40. The LED's 60 can be unlit in the "OFF" state.

When a proximity-indicating output $P_{(A,B)}$ is generated for a given basket electrode (A,B), the processing element 40 switches to an "ON" state the LED 60 that marks the location of the given electrode (A,B) on the hard-wired grid 58. The LED 60, when switched "ON," displays a color, e.g., green, to visually signal to the physician the proximity of the operative element 12 to the given basket electrode (A,B).

It is possible for more than one LED 60 on the hard-wired grid 58 to be switched "ON" at the same time, depending upon the orientation of the operative element 12 to the basket electrodes (A,B) and the spacial sensitivity established for the comparator 46.

(ii) Graphical Display

In a preferred embodiment (see FIG. 6), the output display device 56 comprises a Graphical User Interface (GUI) 62. The GUI 62 is implemented by a graphical control program 82 resident in an external microprocessor based computer control, such as a laptop computer 64 having a keyboard 66, a display screen 68, and mouse 70. The laptop computer 64 is coupled to the processing element 40 (and thus also to the central processing unit 28) via a communication port 72, such as RS 232 or an Ethernet™ connection.

The processing element 40 (or alternatively, the central processing unit 28) conditions the GUI graphical control program 82 to generate on the display screen 68 an idealized graphical image 74, which models the geometry of the particular basket structure 14 deployed in the body region. By reference to this model image 74, the physician is able to visualize the location of each basket electrode (A,B) and spline 20.

In the illustrated and preferred embodiment (see FIGS. 6 and 7), the GUI control program 82 provides a split screen image having a left panel 76 and a right panel 78. The image 74 of the basket structure 14 appears in the left and right panels 76 and 78 as a modeled wire-frame image, with electrodes (A,B) spatially arranged and appearing as nodes 80.

Figure 7:
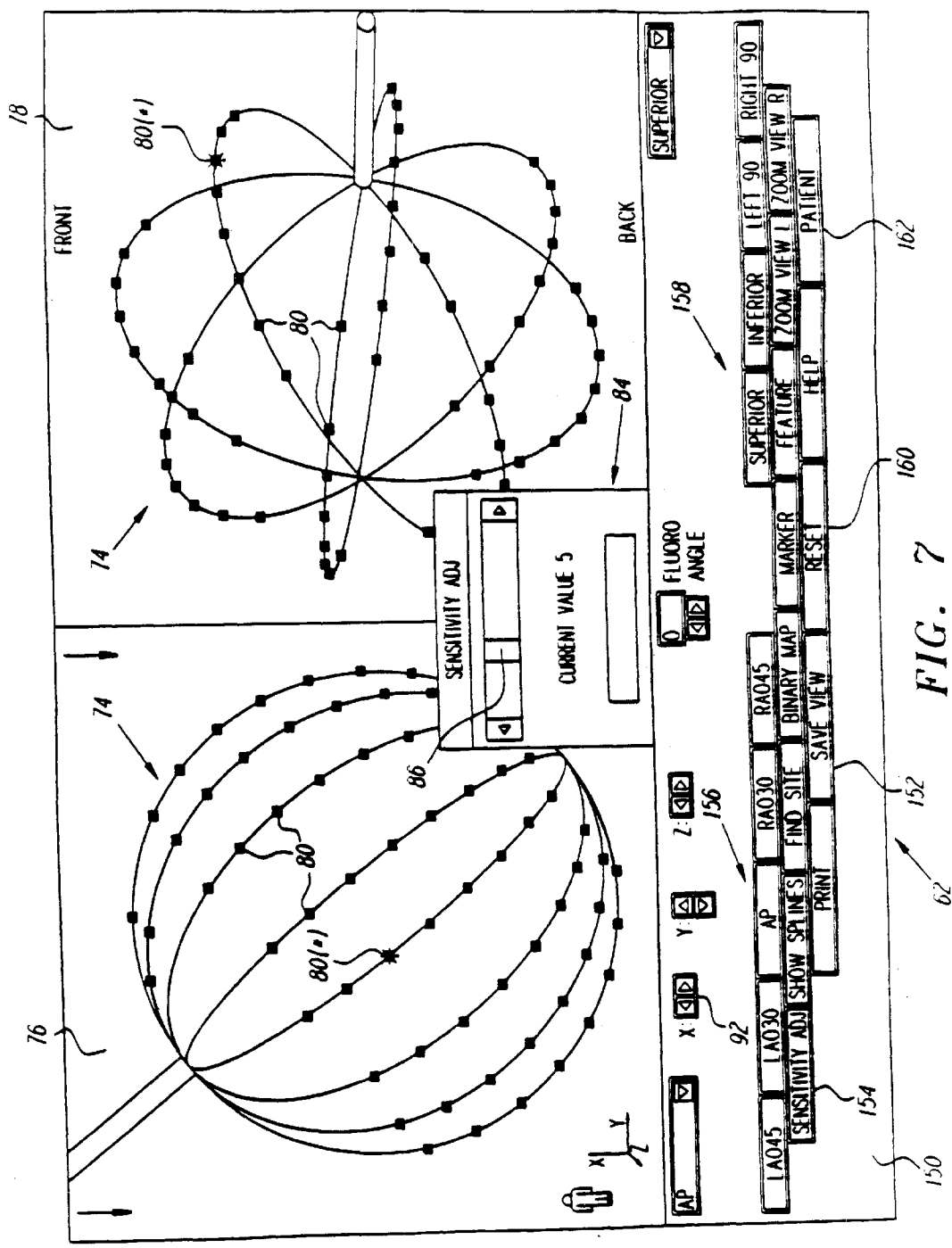
FIG. 7 is a representative view of the split viewing screen of the graphical user interface shown in FIG. 6, showing the idealized model of the three-dimensional basket structure generated by the interface at different idealized orientations.

The panels 76 and 78 make it possible to simultaneously display the image 74 from different idealized orientations. A control program 82 generates an Operational Screen Toolbar 150 (see FIG. 7), which provides the physician with a variety of options to customize the idealized image 74 in each panel 76 or 78. For example (as FIG. 7 shows), the left panel 76 can show the image 74 from a selected oblique angle, such as a right or left anterior angle or a right or left posterior oblique angle, while the right panel 78 can show the image 74 from a selected orthogonal side angle.

In the illustrated embodiment (see FIG. 7), the Toolbar 150 includes an array of View buttons 156. The View Buttons 156 allow the physician to choose among typical orientations for the image 74 in the left panel 76, such as Left 45° or 30° (designated respectively LAO45 LAO30 in FIG. 7), Right 45° or 30° (designated respectively RAO45 RAO30 in FIG. 7), or Anterior/Posterior (designated A/P in FIG. 7). The image 74 in the right panel 78 is consistent with the orientation selected for the image in the left panel, however, another array of View buttons 158 allows the physician to select among typical views for the right panel image, such as Superior, Inferior, Left, and Right.

Thus, by pointing and clicking the mouse 70, or by making command entries using the keyboard 66, the physician is able to set up the desired views in the left and right panels 76 and 78. By clicking the Save View button 152 in the Toolbar 150, the physician is able to save the image in an associated patient data base 128 (see FIG. 9), the details of which will be described later.

A fluoroscope or other imaging device may be used in association with the GUI 62 to visualize the actual orientation of the basket structure 14 and operative element 12 in the body region. The GUI 62 provides a simplified and idealized representation that supplements the fluoroscopic or other independent image.

In the illustrated embodiment, the physician can compare the fluoroscopic or other independent image and manipulate the GUI image 74 to more closely match the view of the fluoroscopic display. To accomplish this (see FIG. 7), the Toolbar 150 includes a set of on-screen X, Y, and Z buttons 92, which can be clicked to cause at least one of the model images 74 to incrementally rotate about idealized X, Y, Z coordinate axes.

In a preferred embodiment, the control program 82 can be controlled by the mouse 70 to change the shape of the idealized image 74 to more closely match the shape of the structure 14 as seen in a fluoroscopic or other independent view. The shape of the image 74 can be formed by dragging the mouse 70, for example, to appear in a range of configurations from spherical to a more elongated ellipsoid (when the structure is a three-dimensional basket structure, as shown in FIG. 1) or to appear in a range of curve radii for an elongated, curvilinear structure (as will be described later). The shape characteristic formed by the physician is saved along with other image information when the save button 152 is clicked.

When saving any image manipulated by use of the Toolbar 150, e.g., to match the particular fluoroscopic or other independent view, the control program 82 allows the physician to uniquely associate the view with one of the preset view buttons 156 or 158, or to create a new custom view button with a custom name for the view. This allows the physician to quickly recall and switch among any view image previously saved. Using the Toolbar 150, the physician can switch views of the graphic image 74 electronically, without manipulating the fluoroscopic display.

The GUI control program 82 initialized the nodes 80 on the model image 74 at a designated color or shade. The initialized color or shade for a given node 80 constitutes a visual signal to the physician, that the operative element 12 is at a "far condition" relative to the associated electrode (A,B).

A proximity-indicating output $P_{(A,B)}$ generated by the processing element 40 for a given electrode (A,B) is transmitted to the control program 82. The control program 82 switches "ON" the node 80(*) marking the location of the given electrode (A,B) in the image 74, by changing the designated color or shade. The node 80, when switched "ON," displays a different color or shade, e.g., green, to visually signal the physician that the operative element 12 is in a "Close Condition" relative to the corresponding basket electrode (A,B).

In the illustrated and preferred embodiment (see FIG. 7), the physician is able to point and click the mouse 70 on a Sensitivity Adjustment button 154 on the Toolbar 150 (or enter commands by the keyboard 66) to open a pop-up Sensitivity Adjustment Window 84. The Window 84 allows the physician to access the input 50 at any point during the procedure, to alter the spacial sensitivity for the proximity-indicating output $P_{(A,B)}$.

In the illustrated embodiment, the Window 84 includes a slide icon 86, which can be dragged by the mouse 70 (or moved by a corresponding keyboard command) between a "Coarse" setting and a "Fine" setting. The "Coarse" setting selects a low-relative value for input 50, in response to which the central processing element 40 sets a $V_{THRESH}$ corresponding to a large-relative nominal distance (for example, at 5 mm). The "Fine" setting selects a high-relative value for input 50, in response to which the processing element 40 sets a $V_{THRESH}$ corresponding to a small-relative nominal distance (for example, at 1 mm). The Window 84 can also displays in alpha/numeric format the current selected nominal distance. The physician is thereby able, in real time during the procedure, to adjust the sensitivity at which the proximity-indicating output $P_{(A,B)}$ is generated, to obtain the desired resolution for the displayed model image 74.

It is possible for more than one node 80 to be switched "ON" at the same time, depending upon the orientation of the operative element 12 to the basket electrodes (A,B) and the spacial sensitivity established. In the illustrated and preferred embodiment (see FIG. 6), the graphical control program 82 includes an interpolating function 88.

Figure 8:
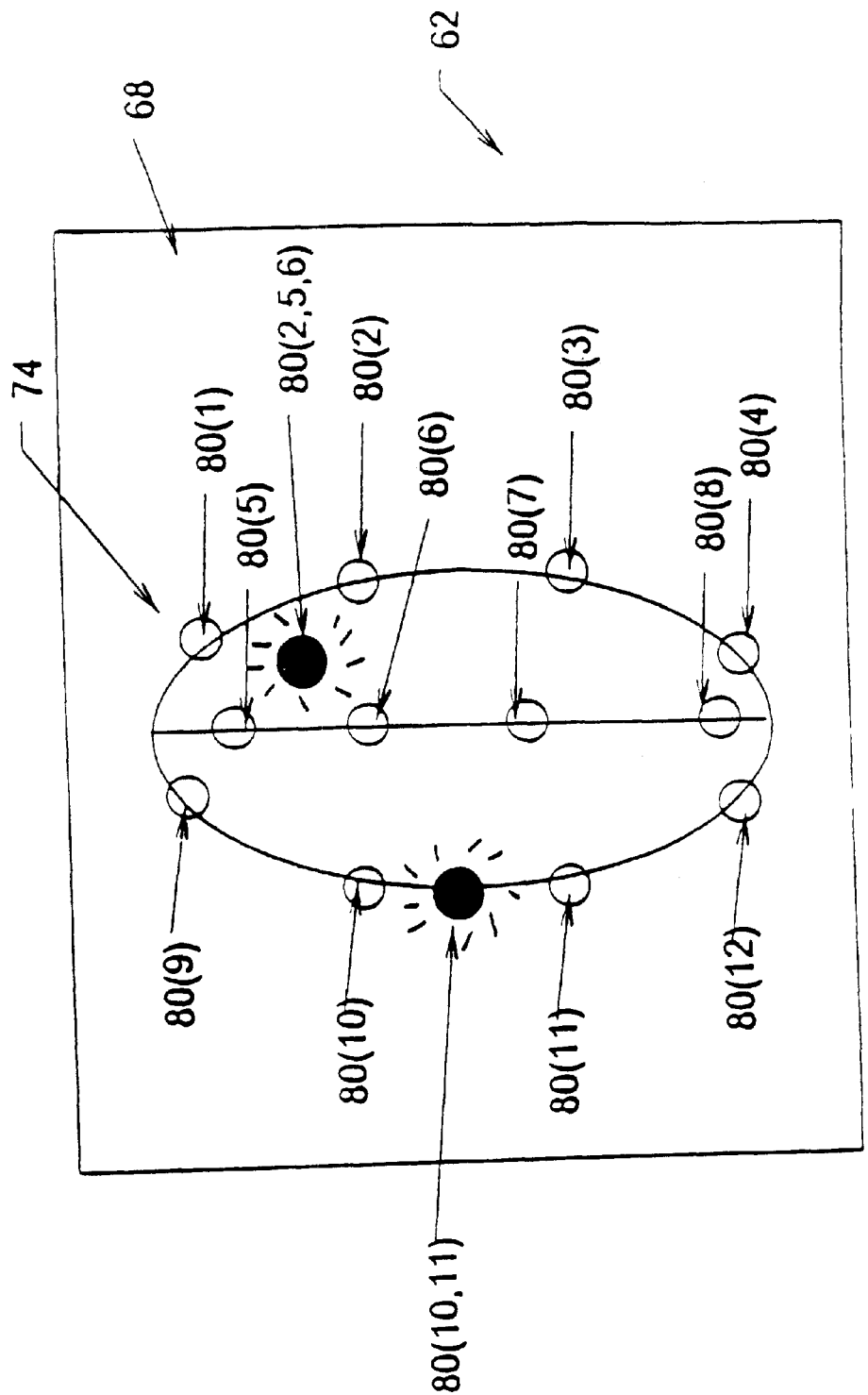
FIG. 8 is a schematic view an idealized model of a three-dimensional basket structure generated by the interface, showing the interpolation of multiple proximity-indicated outputs.

As illustrated in FIG. 8, if two nodes 80 are ordered to be switched "ON" simultaneously (for example, nodes 80(10) and 80(11) in FIG. 8), the interpolating function 88 switches "ON" a phantom node 80(10,11) midway between the two electrode nodes 80.

As also illustrated in FIG. 8, if more than two nodes 80 are ordered to be switched "ON" simultaneously (for example, nodes 80(2), 80(5), and 80(6) in FIG. 8), the interpolating function 88 switches "ON" a phantom node 80(2, 5, 6) at the geometric center of the three or more electrode nodes 80.

Figure 24:
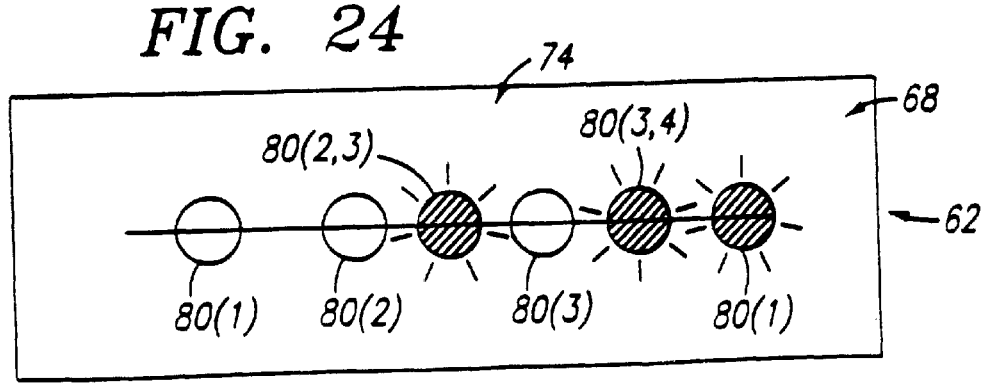
FIG. 24 is a schematic view an idealized model of the spline shown in FIG. 23 generated by the interface, showing the interpolation of multiple proximity-indicated outputs.

FIG. 24 shows an image of several nodes 80(1) to 80(4), corresponding to the arrangement of electrodes 22(1) to 22(4) along a single spline 20 shown in FIG. 23. In the FIG. 23 embodiment (as previously described), the electrodes 22(1) to 22(4) serve as the transmitting electrodes, and they are energized simultaneously. As shown in FIG. 23 (and as previously described), the roving element 12 carries multiple sensing electrodes 30(1), 30(2), and 30(3). The generation of multiple, simultaneous proximity-indicating outputs (as previously described) orders node 80(4) to be switched "ON" due to its close condition to both roving electrode 30(1) and 30(2); node 80(3) to be switched "ON" due to its close condition to both roving electrodes 30(2) and 30(3); and node 80(2) switched "ON" due to its close condition to roving electrode 30(3). The interpolating function 88 switches "ON" phantom nodes (3,4) and (2,3) midway between the nodes (2) and (3) and midway between the nodes (3) and (4). As FIG. 24 shows, switched "ON" node (4) and the switched "ON" phantom nodes (3,4) and (2,3) collectively create a pattern that matches both the actual position and general orientation of the roving electrodes 30(1) to 30(3) relative to the electrodes 22(1) to 22(4), as shown in FIG. 23.

The display of the proximity-indicating outputs $P_{(A,B)}$ continuously tracks movement of the roving electrode 30 and electrodes 30(1), 30(2) and 30(3) relative to the electrodes (A,B) on the structure 14.

E. Electrically Identifying Structures

The system 10 can be used in association with a family of basket structures 14. Basket structures 14 within the family are characterized by different physical properties, such as the size of the structure 14; the shape of the structure 14; the radial symmetry or asymmetry of the structure 14; the axial symmetry or asymmetry of the structure 14; the number of spline elements 20; the total number of electrodes 22 carried by the structure 14; the number of electrodes 22 carried per spline element 20; the distance between electrodes 22 on each spline element 20; the distribution or density pattern of electrodes 22 on the structure 14; or combinations thereof.

Figure 6:
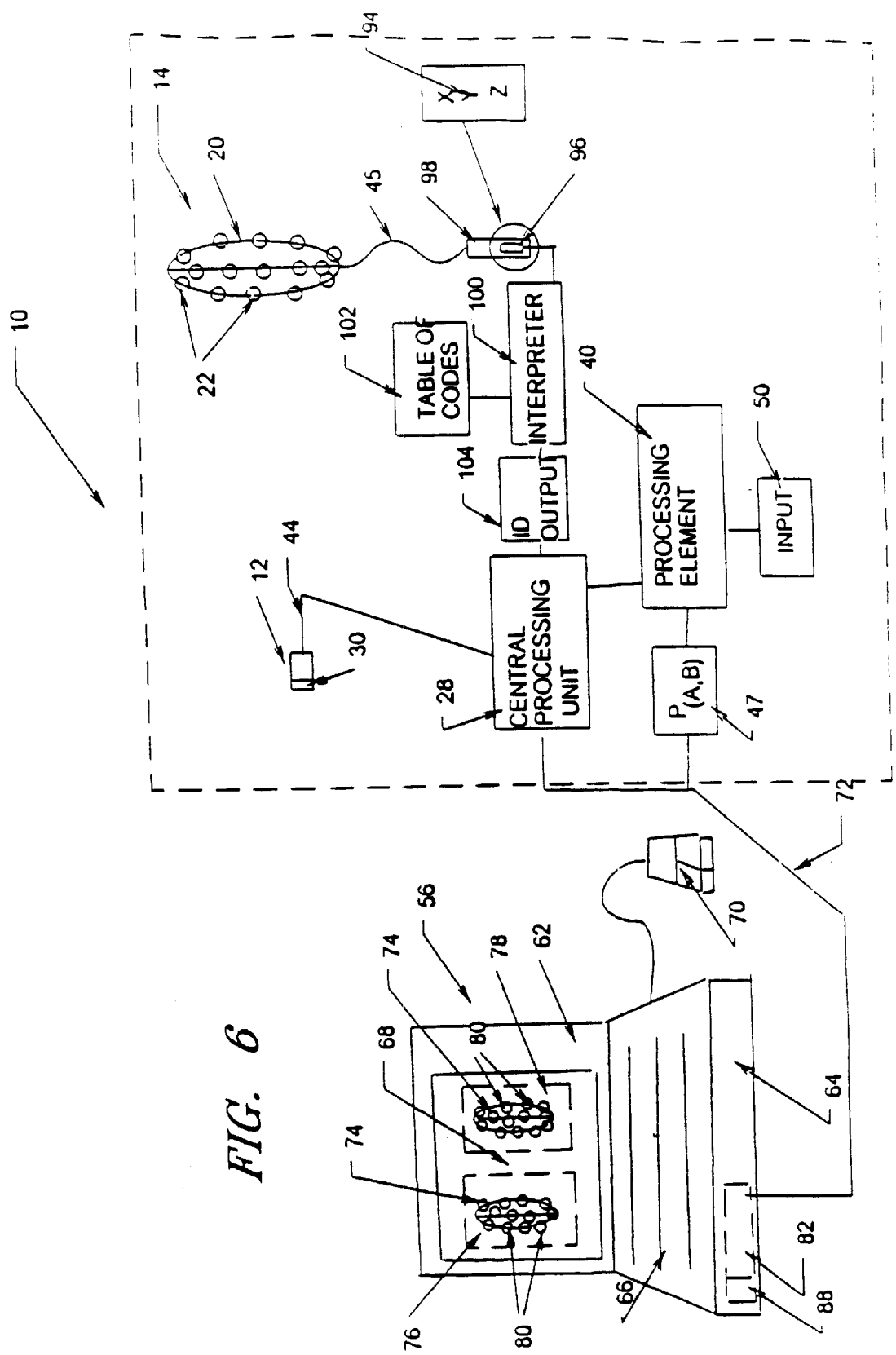
FIG. 6 is a schematic view of an embodiment of a graphical user interface used by the system to visually display the presence or absence of a proximity-indicated output at each electrode carried by the three-dimensional basket structure.

As FIG. 6 shows, the system 10 includes identification codes 94 to identify individual basket structures 14 within the family of basket structures. Each identification code 94 uniquely identifies a particular basket structure 14 in terms of its physical property or properties.

As FIG. 6 shows, the code 94 is carried by a coded component 96, which is attached in association with each basket structure 14. In the illustrated embodiment, the coded component 96 is located within a handle 98 attached at the proximal end of the catheter tube 45 that carries the basket structure 14. However, the component 96 could be located elsewhere on the catheter tube 45 or structure 14. The code 94 can also be manually inputted by the physician using the keyboard 66.

The coded component 96 can be variously constructed. It can, for example, take the form of an integrated circuit, which expresses in digital form the code 94 for input in ROM chips, EPROM chips, RAM chips, resistors, capacitors, programmed logic devices (PLD's), or diodes. Examples of catheter identification techniques of this type are shown in Jackson et al. U.S. Pat. No. 5,383,874, which is incorporated herein by reference.

Alternatively, the coded component 96 can comprise separate electrical elements, each one of which expresses an individual characteristic. For example, the component 96 can comprise several resistors having different resistance values. The different independent resistance values express the digits of the code 94.

The coded component 96 is electrically coupled to an external interpreter 100 when the basket structure 14 is plugged into the central processing unit 28 for use. The interpreter 100 inputs the code 94 and electronically compares the input code 94 to, for example, a preestablished master table 102 of codes contained in memory. The master table 102 lists, for each code 94, the physical characteristics of the structure 14. The interpreter 100 generates a identification output 104 based upon the table 102. The graphical control program 82 retains a library of idealized graphical images that reflect the different geometries identified by the output 104. Based upon the identification output 104 received from the central processing unit 28, the control program 82 generates the particular idealized graphical image 74 that corresponds to the geometry of the particular basket structure 14 in use.

F. Use With Cardiac Diagnosis and Treatment Systems

Figure 9:
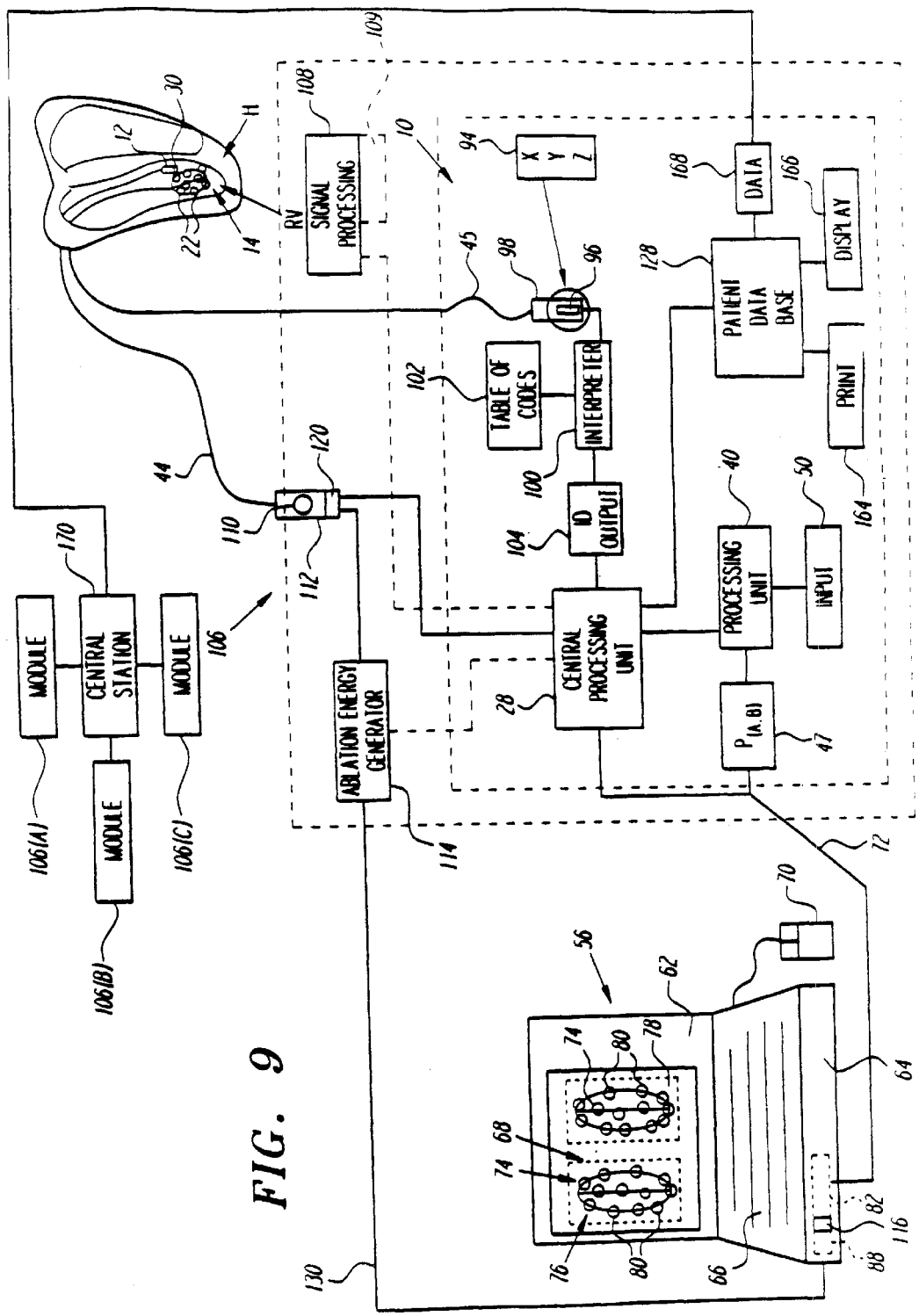
FIG. 9 is a schematic view of the system shown in FIG. 1 as part of a modular system used to diagnose and treat cardiac conditions.

In a preferred embodiment (see FIG. 9), the system 10 forms a part of a modular system 106, which is used to diagnose and treat abnormal cardiac conditions. FIG. 9 shows a representative embodiment of the modular system 106 of which the system 10 forms a part. Additional details of the modular system 106 not material to the invention can be found in co-pending application Ser. No. 08/813,624, entitled "Graphical User Interface for Use with Multiple Electrode Catheters," filed Mar. 7, 1997, now U.S. Pat. No. 5,916,163.

In FIG. 9, the basket structure 14 and operative element 12 are shown deployed and ready for use within a selected region inside a human heart H. FIG. 9 generally shows the basket structure 14 and operative element 12 deployed in the right ventricle RV of the heart H. Of course, the basket structure 14 and element 12 can be deployed in other regions of the heart, too. It should also be noted that the heart shown in the FIG. 9 is not anatomically accurate. FIG. 1 shows the heart in diagrammatic form to demonstrate the features of the invention.

In FIG. 9, the basket structure 14 and element 12 have each been separately introduced into the selected heart region through a vein or artery (typically the femoral vein or artery) through suitable percutaneous access. Alternatively, the basket structure 14 and operative element 12 can be assembled in an integrated structure for simultaneous introduction and deployment in the heart region.

Further details of the deployment and structures of the basket structure 14 and element 12 are set forth in pending U.S. patent application Ser. No. 08/033,641, filed Mar. 16, 1993, entitled "Systems Using Guide Sheaths for Introducing, Deploying, and Stabilizing Cardiac Mapping and Ablation Probes," now U.S. Pat. No. 5,636,634.

The electrodes (A,B) carried by the basket structure 14 are electrically coupled to a signal processing system 108. The electrodes (A,B) sense electrical activity in heart tissue. The sensed activity is processed by the processing system 108 to assist the physician in identifying the site or sites within the heart appropriate for ablation. This process, called mapping, can be accomplished in various way, according to the choice of the physician.

For example, the physician can condition the processing system 108 to take multiple, sequential measurements of the transmission of electrical current by heart tissue to obtain tissue resistivity measurements. The processing of tissue resistivity signals to identify appropriate ablation sites is disclosed in co-pending U.S. patent application Ser. No. 08/197,236, filed Jan. 28, 1994, and entitled "Systems and Methods for Matching Electrical Characteristics and Propagation-Velocities in Cardiac Tissue to Locate Potential Ablation Sites," now abandoned.

Alternatively, or in conjunction with tissue resistivity measurements, the physician can condition the processing system 108 to acquire and process electrograms in a conventional fashion. The processing system 108 processes the electrogram information to map the conduction of electrical impulses in the myocardium.

The identification code 94 previously described can also identify a functional property of the electrodes (A,B) on the basket structure 14 in terms of a diagnostic capability, such as mapping, or derivation of an electrical characteristic, or pacing. The processing system 108 can include functional algorithms 109, which set operating parameters based upon the code 94. For example, the code 94 can provide input to tissue mapping algorithms to enable early activation detection, or fractionation mapping, or pace mapping, or entrainment pacing. The code 94 can also provide input to electrical characteristic derivation algorithms, or provide interpolation for evaluating electrograms between electrodes, or extrapolate sensed electrical activities to locate potential ablation sites.

The electrode 30 on the operative element 12 also serves as an ablation electrode. Of course, other configurations employing multiple ablation electrodes are possible, as described in pending U.S. patent application Ser. No. 08/287,3 10, filed Aug. 8, 1994, entitled "Systems and Methods for Forming Large Lesions in Body Tissue Using Curvilinear Electrode Elements," now U.S. Pat. No. 5,582,609.

A catheter tube 44 which carries the operative element 12 includes a steering mechanism 110 contained within a proximal handle 112 (see FIG. 2B also). As FIG. 2B shows, the steering mechanism 110 selectively bends or flexes the catheter tube 44 to bring the operative element 12 and ablation electrode 30 into conforming, intimate contact against the endocardial tissue. Details of the steering mechanism are shown in U.S. Pat. No. 5,254,088, which is incorporated herein by reference.

The ablation electrode 30 is electrically coupled to a generator 114 of ablation energy. The type of energy used for ablation can vary. Typically, the generator 114 supplies electromagnetic radio frequency energy, which the electrode 30 emits into tissue.

The operative element 12 can also carry a code 120, in the same manner as the code 94 is carried by the basket structure 14. The code 120 identifies the physical characteristics of the element 12, such as its diagnostic function or its therapeutic functions. The code 120 can also identify the physical characteristics of the ablation electrode 30, such as its size and the presence or absence of temperature sensing capabilities. Based upon the code 120, the central processing unit 28 can condition the ablation energy supply functions of the generator 114, such as by setting maximum or minimum power, and enabling specialized ablation control algorithms, e.g., by tissue temperature sensing.

The physician places the ablation electrode 30 in contact with heart tissue at the site identified by the basket structure 14 for ablation. The ablation electrode 30 emits ablating energy to heat and thermally destroy the contacted tissue.

The system 10 is electrically coupled to the basket structure 14 and the operative element 12, as already described. The system 10 collects and processes information to generate proximity-indicating outputs $P_{(A,B)}$ regarding the proximity of the ablation electrode 30 relative to the electrodes (A,B) on the structure 14. The display of the proximity-indicating outputs $P_{(A,B)}$ as previously described, wither on the hardware grid 58 or the GUI 62, continuously tracks movement of the ablation electrode 30 relative to the electrodes (A,B) on the structure 14. The display of the proximity-indicating outputs $P_{(A,B)}$ thereby aids the physician in guiding the ablation electrode 30 into contact with tissue at the site identified for ablation.

G. Patient Data Base

In a preferred embodiment (see FIGS. 9, 10A, and 10B), the graphical control program 82 includes a MARKERS function 116. The MARKER function 116 enables the physician to alter and enhance the displayed model image 74 of the basket structure 14.

Figure 10A:
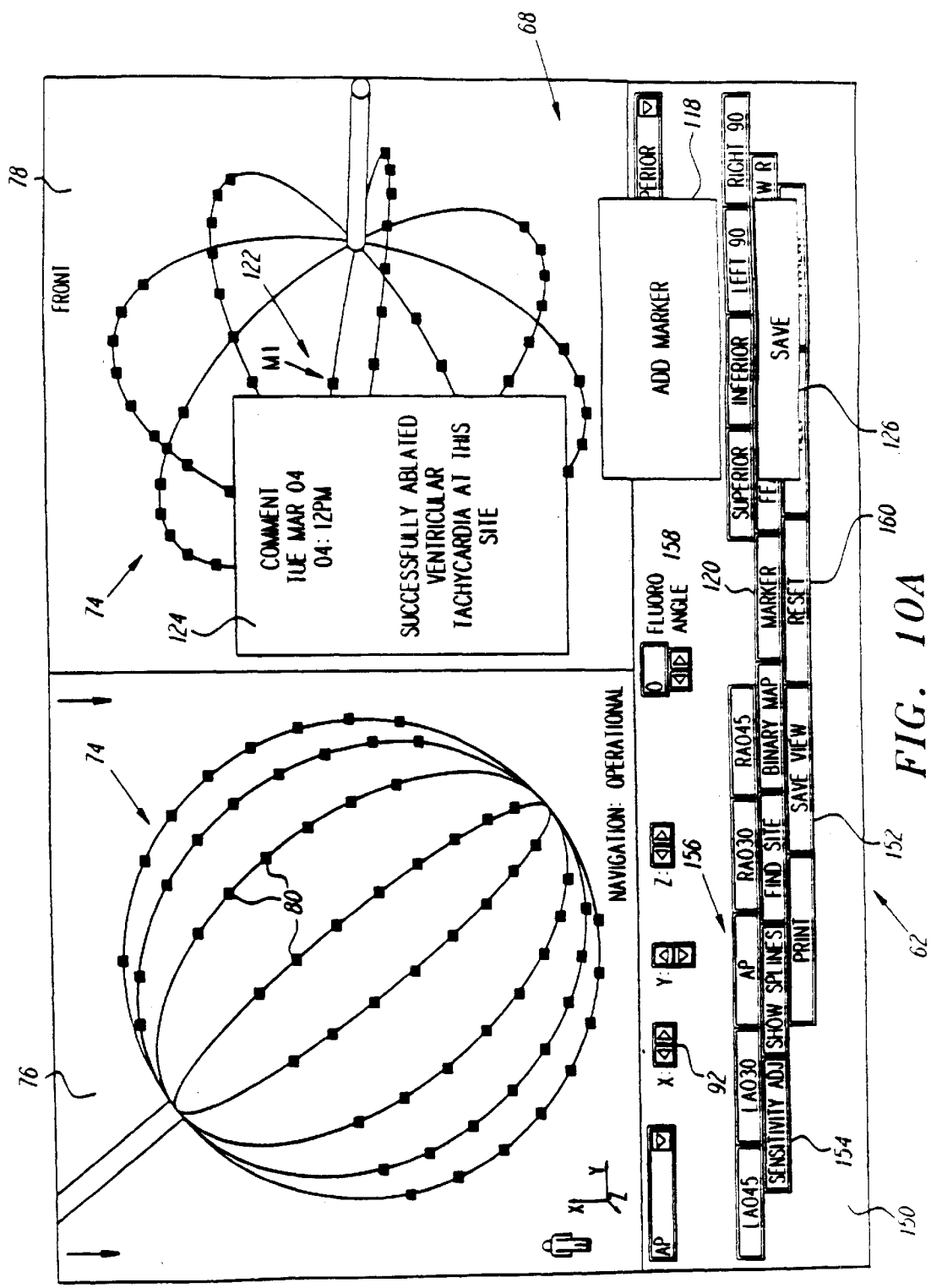
FIGS. 10A and 10B are representative views of the split viewing screen of the graphical user interface shown in FIG. 9, showing the use of markers and comments in association with the idealized model of the three-dimensional basket structure that the interface generates.

The MARKERS function 116 enables the operator to annotate the image by adding an identifier or marker to selected locations of the image 74. As FIG. 10A shows, the MARKERS function 116 is activated by clicking the ADD MARKER button 118 that appears on the screen 68 after the general "MARKERS" button 120 is clicked on the Toolbar 150. Pressing the right mouse button on an electrode (A,B) causes a marker 122 to appear on the screen. With the right mouse button depressed, the physician can "drag" the marker 122 to the desired location. When the right mouse button is released, the marker 122 is "dropped" into the desired marker location.

The MARKERS function 116 also enables the physician to add custom annotations in the form of notes or comments to each marker 122. As FIG. 10A shows, a COMMENT window 124 appears as soon as the marker 122 is "dropped" at the selected site. A time stamp is preferably automatically included in the comment window 124. The operator can enter the desired comment into the comment window 124 using the computer keyboard.

Figure 10B:
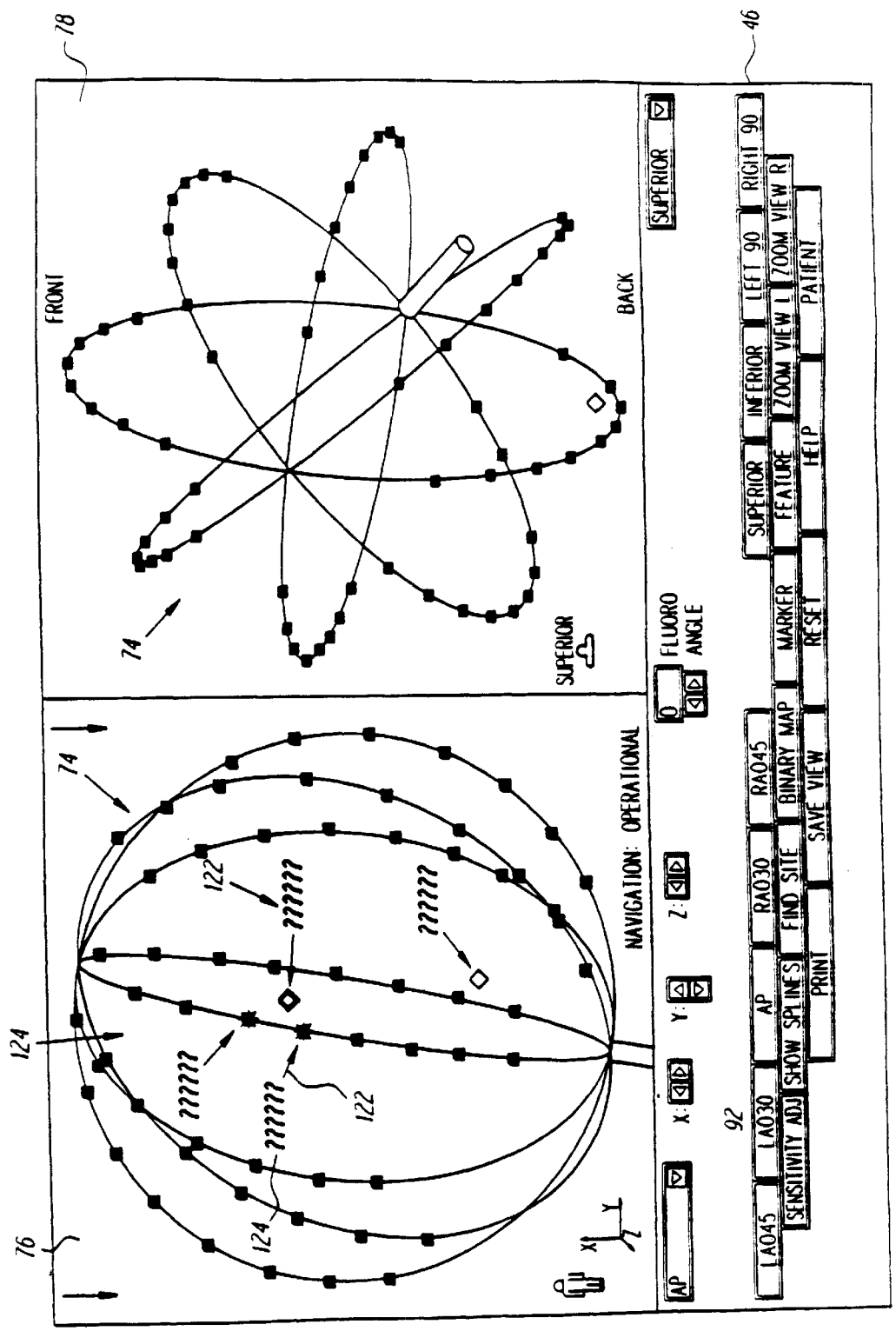

As FIG. 10B best shows, markers 122 and comments 124 can be placed near electrodes on either the foreground or background of the image 74, e.g., to mark selected locations that are significant or of interest, such as mapping sites, ablation sites, etc. The physician is thereby better able to remain coordinated and oriented with the displayed image and, therefore, better able to interpret data recovered by the basket structure 14.

By clicking a pop up SAVE button 126 (or alternatively, clicking the Save View button 152 on the Toolbar 150) at desired times, the entire graphical display, including model image 74, markers 122, and associated comment windows 124 can be saved as a data file record for storage, retrieval, or manipulation. The physician is thereby able to create during a given diagnostic or therapeutic procedure a patient-specific data base 128, stored in on board memory, which records the diagnostic or therapeutic events of the procedure. Further details about the patient data base 128 will be described later.

In the illustrated embodiment (see FIG. 9), a control line 130 couples the generator 114 to the graphic control software 82. Transmission of ablation energy by the generator 114 generates an output signal in the control line 130. The output signal commands the control program 82 to automatically save the entire graphical display as it exists at the instant ablation occurs. The physician is thereby able to record each ablation event in the context of a graphical image for inclusion in the data base 128 specific to the patient.

The output signal commands identification of the location of the ablation electrode, generates a time stamped marker 122, and generate an ablation-indicating annotation, e.g., a comment window 124 or marker 122, identifying the position of the electrode at the instant ablation occurs.

Figure 11:
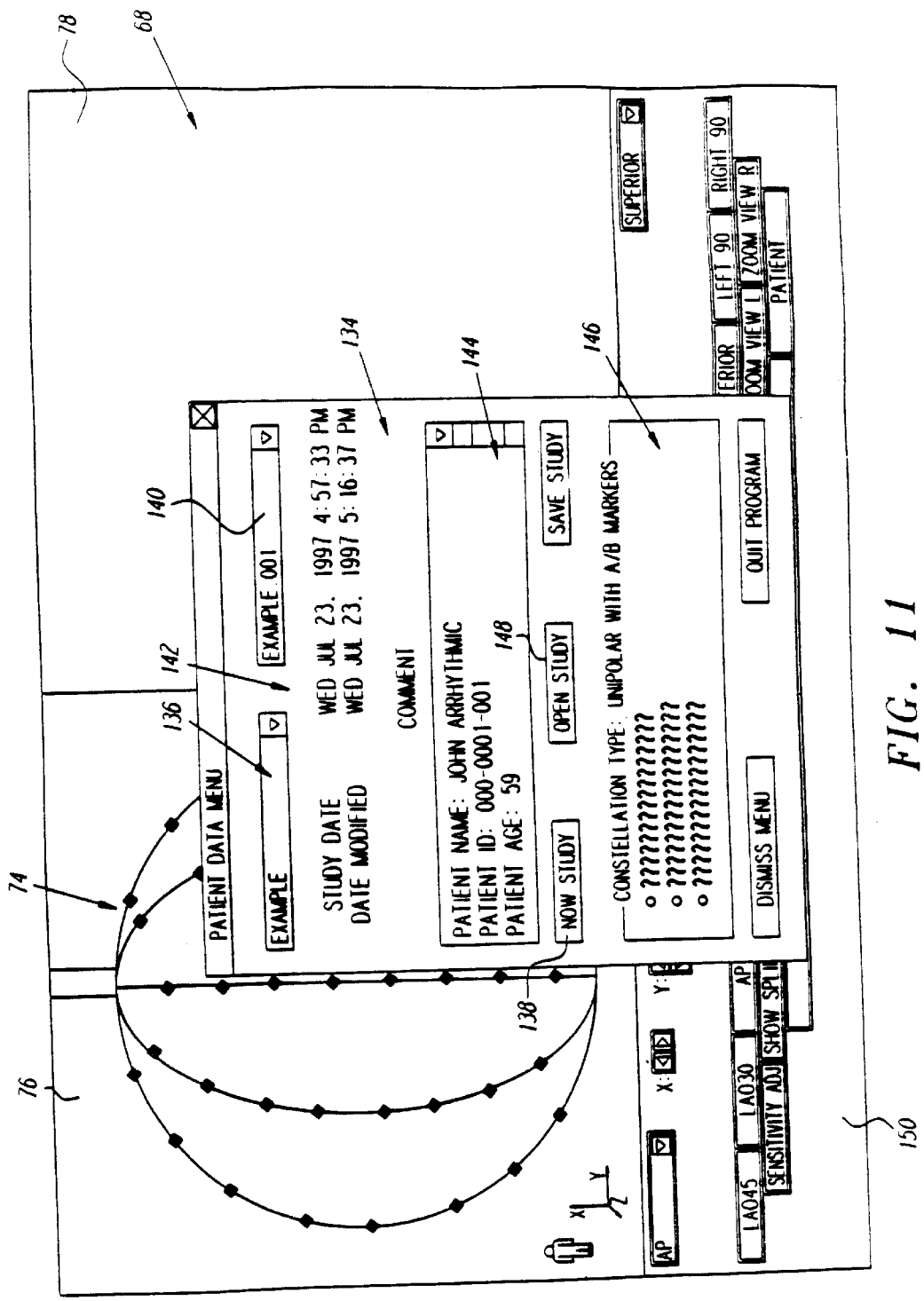
FIG. 11 is a representative view of the viewing screen of the graphical user interface shown in FIG. 9, showing the pop up Patient Data Menu used to establish and maintain a patient-specific data base.

To establish and maintain records in the patient data base 128, the graphical control program 82 includes a PATIENT DATA function 132. As FIG. 11 shows, at the time that the control program 82 generates the Operational Screen Toolbar 150 (previously described), the control program 82 also opens a Patient Data Window 134. The Patient Data Window 134 allows the physician to enter data about the particular patient and thereby make patient specific subsequent information recorded and saved in the data base 128.

To create a patient-specific record in the data base 128, the physician enters in the Patient field 136 of the Window 134 the name of the patient and clicks the New Study button 138. The control program 82 enters a default file name in a Study Name field 140, with associated time marker 142. The physician can enter in the Text field 144 additional information or comments regarding the patient, such as the patient's ID number, age, etc, which the physician wants to save as part of the patient record. The physician can also enter diagnostic information, e.g., heart tissue pacing data; or therapeutic information, e.g., heart tissue ablation data; or identify the attending physician or staff personnel. The physician can also select in the Device field 146 the type of structure 14 that will be deployed in the patient. The physician can then click the Open Study button 148 to begin the new study.

When beginning a new study, the control program 82 gives the physician the option of starting the new study with new image views in the left and right panels 76 and 78 (by clicking the Reset button 160 on the Toolbar 150, as shown in FIG. 7). The Toolbar 150, previously described, allows the physician to customize the left and right panel images 74 for the new study, in the manner previously described in connection with FIG. 7.

Alternatively, the control program 82 gives the physician the option of using the same image views set in an immediately preceding study. This option allows the physician to quickly switch among different diagnostic or therapeutic protocols (each constituting a "study") on the same patient using the same structure 14 in the same heart chamber.

During a given study, the physician can implement the MARKERS function 116 to set up markers 122 and comment windows 124 in association with the selected image views, as FIGS. 10A and 10B show. In the comment windows 124, the physician can include further information identifying the procedure, diagnostic information, therapeutic information, or otherwise annotate the image. By clicking the SAVE view button 126 on the Toolbar 150 at desired times, the entire graphical display, including model image 74, markers 122, and associated comment windows 124 are saved as a data file uniquely associated for the particular study and particular patient for storage, retrieval, or manipulation. The control program 82 gives the physician the option of protecting the data by use of a password, to restrict access to all or some of the data base records.

As FIG. 9 shows, an output device, such as a printer 164 or graphics display terminal 166, allows patient record information to be recalled or down loaded for off-line analysis or compilation. The patient record will contain the entire graphical image 74 (including shape characteristics or orientations added by the physician), markers 122, and associated comment windows 124 in existence at the time the record was saved. As FIG. 11 shows, the patient study Window 134 can with time markers 142 provide information documenting the storage, retrieval, or manipulation of the data base record, such as the date on which data in the record is entered or updated, or the date on which data was retrieved or otherwise manipulated.

As FIG. 9 also shows, a communications port 168 allows patient record information to be transmitted to a central data storage station 171. A network of local or remote systems 106, 106(A), 106(B), and 106(C), each having all or some of the features described for module 106, can be linked to the central data storage station 171, by an Internet-type network, or by an intranet-type network. The network of work station modules 106, 106(A), 106(B), and 106(C), all linked to the central data storage station 171, allows patient-specific data base records for many patients at one or more treatment facilities to be maintained at a single location for storage, retrieval, or manipulation.

To exit the control program 82, the physician clicks the Patient/Quit button 162 on the Toolbar 150 (see FIG. 7).

II. Proximity sensing Using Other Structures

A. Elongated Structures

Figure 12:
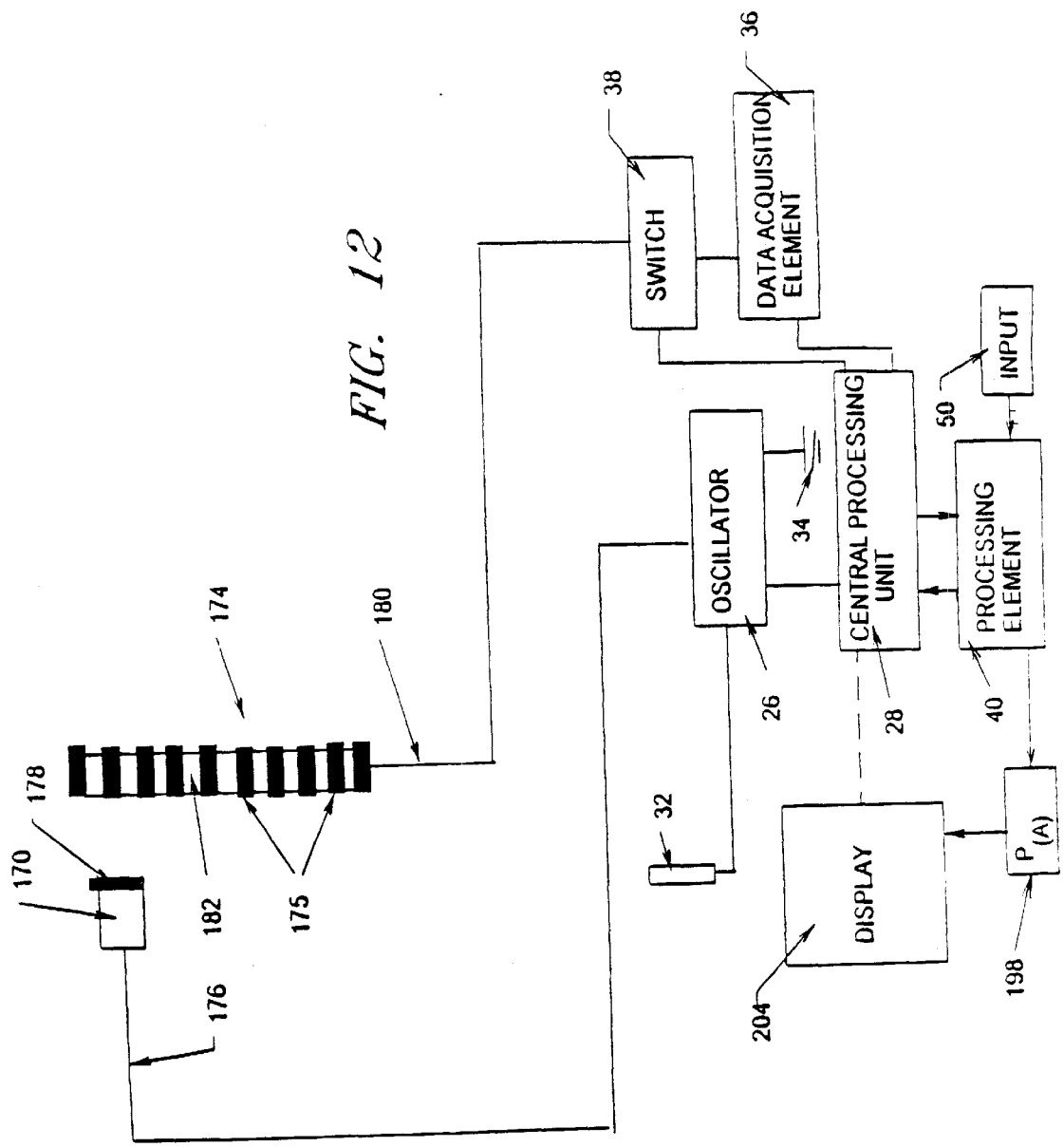
FIG. 12 is a schematic view of a system for sensing the position of an operative element with respect to an elongated electrode array.

FIG. 12 shows another embodiment of a position sensing system, which locates the position of an operative element 170 along a locating probe. In FIG. 12, the locating probe takes the form of an elongated electrode array 174.

The operative element 170 is constructed in the same way as the element 12 previously described and shown in FIG.

Figure 13:
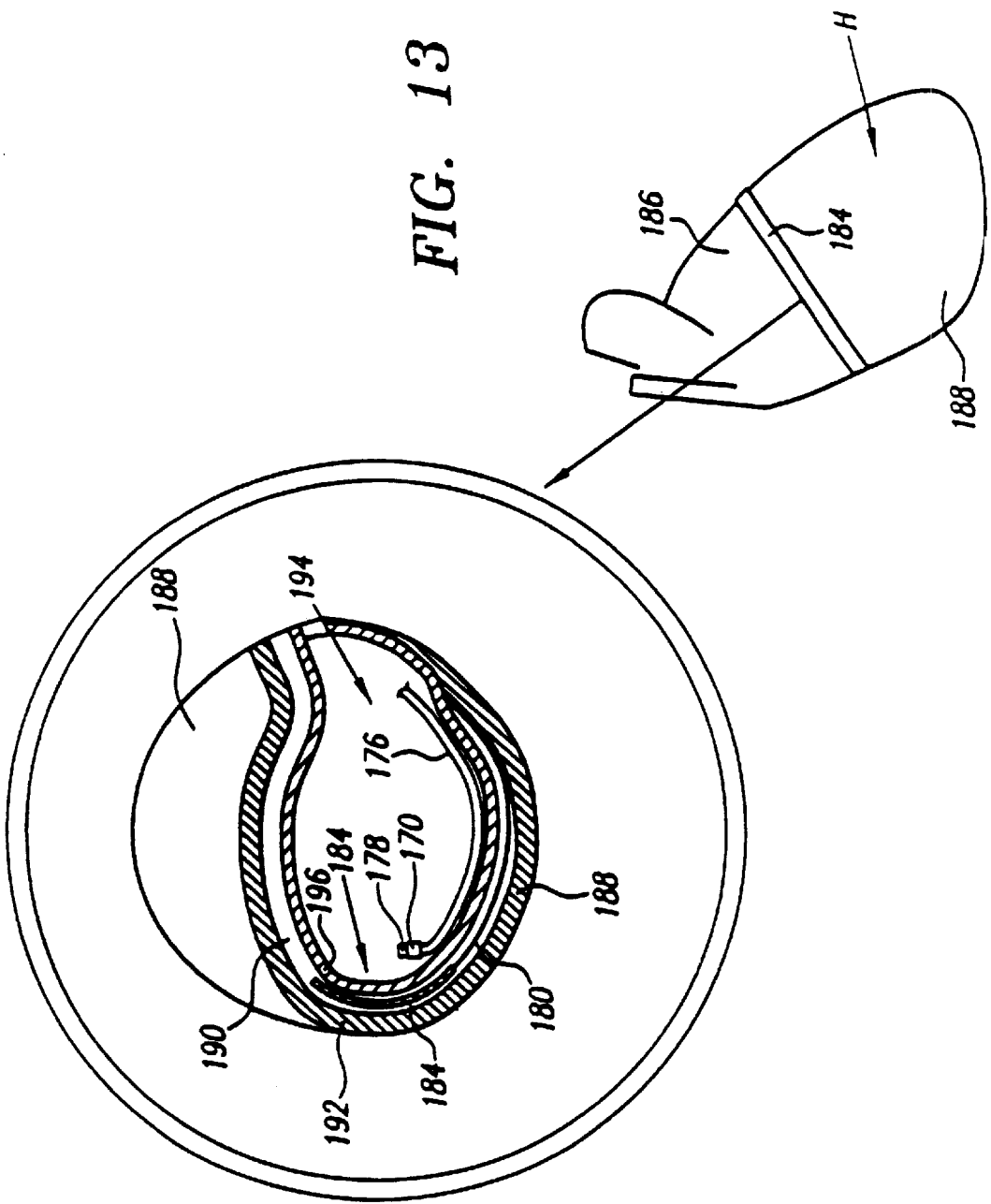
FIG. 13 is a diagrammatic view of the operative element and elongated electrode array shown in FIG. 12 deployed for diagnostic or therapeutic purposes in the annulus region of a human heart.

2B. As FIG. 13 shows, the element 170 is carried at the distal end of a catheter tube 176. However, like the element 12, the element 170 need not be necessarily catheter-based.

As earlier described, the operative element 170 can be used for either therapeutic purposes, or diagnostic purposes, or both. In the illustrated embodiment, the operative element 170 includes an electrode 178, which can be conditioned to sense a physiological characteristic in myocardial tissue. The electrode 178 can also be conditioned to transmit electrical energy to stimulate (i.e., pace) myocardial tissue, as well as transmit radio frequency energy to ablate myocardial tissue.

As shown in FIG. 12, the elongated array of electrodes 174 are also carried at the distal end of a catheter tube 180 in the same way that the structure 14 is carried by a catheter tube 45 in FIG. 2A. In the illustrated embodiment, the electrodes 174 take the form of conventional rings 175 of electrically conductive material (e.g., copper alloy, platinum, or stainless steel), arranged in a spaced apart, segmented relationship about a sleeve 182 of electrically insulating material. Alternatively, the electrodes 174 can be coated upon the sleeve 182 using conventional coating techniques or an ion beam assisted deposition (IBAD) process, or comprise spaced apart lengths of wound, spiral coils made of electrically conducting material.

In the illustrated embodiment, the distal regions of both catheter tubes 176 and 180 can be flexed using an on board steering mechanism (not shown). The feature has been previously described in association with the first described embodiment and is shown in FIGS. 2A and 2B.

FIG. 13 shows the operative element 170 and array of electrodes 174 deployed in the annulus region 184 of a human heart H. FIG. 13 shows the deployment diagrammatically and not with anatomic precision.

The annulus region 184 lays at the intersection of the atrial structure 186 and the ventricular structure 188 of the heart. The annulus region 184 is a site where the electrophysiological source of many arrhythmias can be mapped and successfully eliminated by ablation.

In FIG. 13, the operative element 170 and its electrode 178 are shown deployed inside an atrium 194 near the annulus region 184. The physician is able to selectively move the element 170 along the endocardial surface 196 inside the atrium at or near the annulus region 184.

As shown in FIG. 13, the elongated array of electrodes 174 is deployed outside the atrium 194, within an adjacent region of the great cardiac vein 190. The great cardiac vein 190 is a fixed anatomic structure, which extends close to the epicardium 192 along the annulus region 184. The great cardiac vein 190 thereby serves as an anatomic marker to aid the physician in situating the locating array of electrodes 174 in the annulus region 184.

As FIG. 12 shows, and functioning in the same manner as previously described with reference to FIG. 1, the central processing unit 28 conditions the oscillator 26 to transmit an electrical AC waveform through the electrode 178 carried by the operative element 170. The indifferent electrode 32 comprises the voltage return, coupled to an electrical reference, which, in the illustrated embodiment, is isolated or patient ground 34. The voltage field that is created varies in detected amplitude at each electrode ring 175 according to its distance from the electrode 178 carried by the operative element 170. A proximity-indicating output 198 (designated $P_{(A)}$) is generated in the manner previously described for a given electrode ring 175 (where A equals 1 to the number of electrode rings 175 on the array 174), when the prescribed "close condition" between the given ring electrode 175 and the electrode 178 exists.

Figure 14:
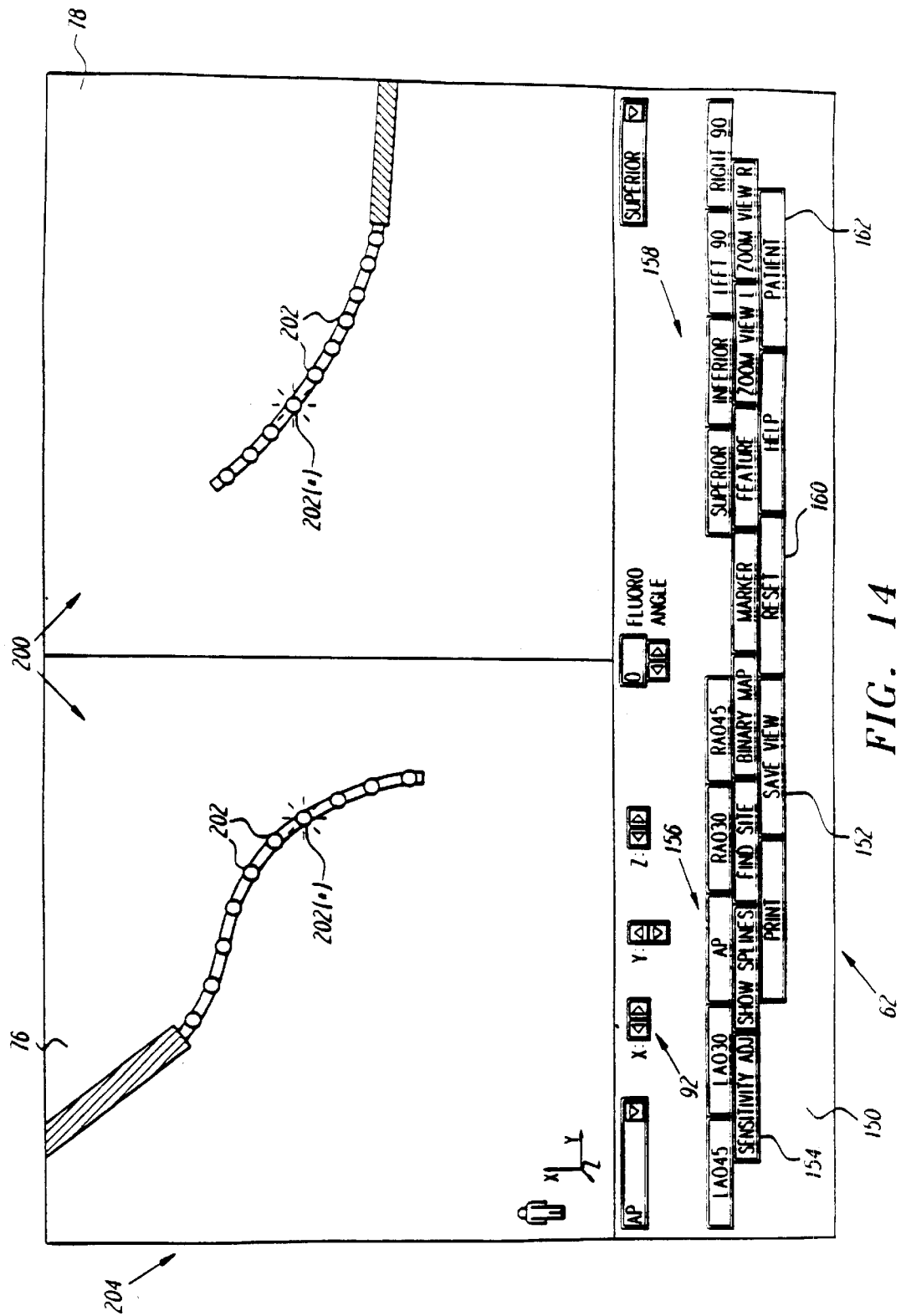
FIG. 14 is a schematic view of an embodiment of a Graphical user interface used by the system shown in FIG. 12 to visually display the presence or absence of a proximity-indicated output at each electrode carried by the elongated electrode array.

Since the position and orientation of the great cardiac vein 190 is known, a graphic display 204 can generate an idealized graphical image 200 (see FIG. 14) for the electrode array 174, in which nodes 202 mark the ring electrodes 175. The display 204 thereby graphically depicts for the physician an idealized graphical image of the portion of the annulus region 184 where the electrode array 174 is deployed.

Using the ring electrodes 174, the physician can pace and sense electrical events in myocardial tissue along the annulus region 184. In tandem, the physician can also pace and sense using the electrode 178 on the operative element 170. Pacing and sensing both inside and outside the atrium 194 permit the detection of differences between electrophysiological activities near the epicardial surface (detected by the ring electrodes 175) and near the endocardial surface (detected by the electrode 178). This differential detection technique provides advanced diagnostic capabilities.

Generation of the proximity-indicated output 198 (as previously described with reference to the basket structure 14) switches "ON" the node 202 when the prescribed "close condition" to the roving electrode 178 exits. The display 204 thereby tracks the movement of the roving electrode 178 along the annulus region 184 as mapping and diagnostic functions proceed.

Once mapping identifies a candidate ablation site, the display 204 aids the physician in moving the electrode 178 to the site for the purpose of transmitting ablation energy.

B. Loop structures

Figure 15:
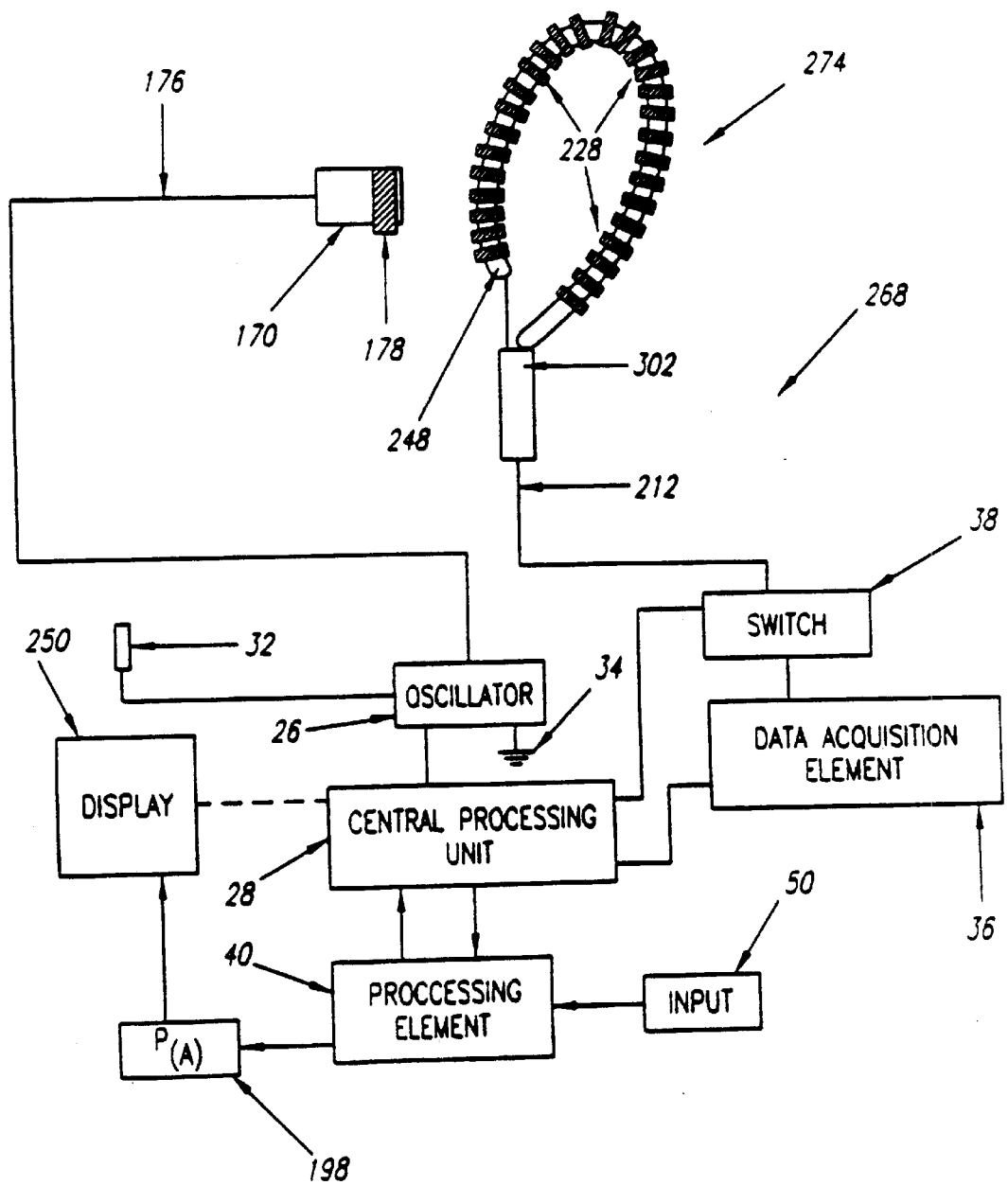
FIG. 15 is a schematic view of a system for sensing the position of an operative element with respect to a multiple electrode loop structure.

FIG. 15 shows still another embodiment of a position sensing system 268 to locate the position of the same or equivalent operative element 170 and associated electrode 178 shown and described in connection with the FIG. 13 embodiment. In this embodiment, the locating probe comprises a multiple electrode loop structure 274.

The loop structure 274 can be constructed in various ways. In the illustrated embodiment (see FIGS. 16 and 17), the structure 274 is formed from a core spline leg 246 covered with an electrically insulating sleeve 248. Multiple electrode elements 228 are secured on the sleeve 248.

In the illustrated embodiment, the electrodes 228 take the form of conventional rings of electrically conductive material (e.g., copper alloy, platinum, or stainless steel), arranged in a spaced apart, segmented relationship about the sleeve 248. As previously described in connection with the electrode array 174, the electrodes 174 can, in an alternative construction, be coated upon the sleeve 248, or comprise spaced apart lengths of wound, spiral coils made of electrically conducting material.

Figure 17:
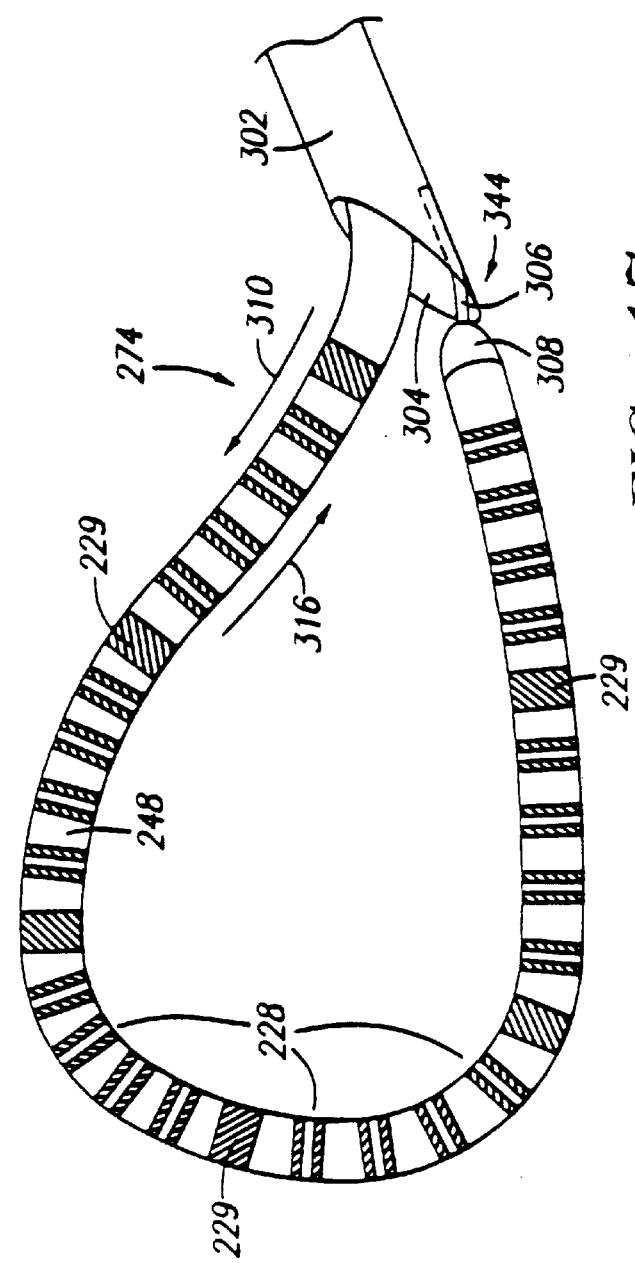
FIG. 17 is a perspective view of the multiple electrode loop structure shown in FIG. 16, with the loop structure deployed for use beyond the associated sheath.

As demonstrated in FIG. 17, the ring electrodes 228 can be arranged in a prearranged pattern. In FIG. 17, the pattern comprises paired groups of eight electrodes 228, separated by enlarged spacer rings 229. The pattern assists the physician to orient the structure 274 when viewing it fluoroscopically.

The number of electrodes 228 can vary. Typically, between 10 and 24 electrodes 228 are used.

Figure 16:
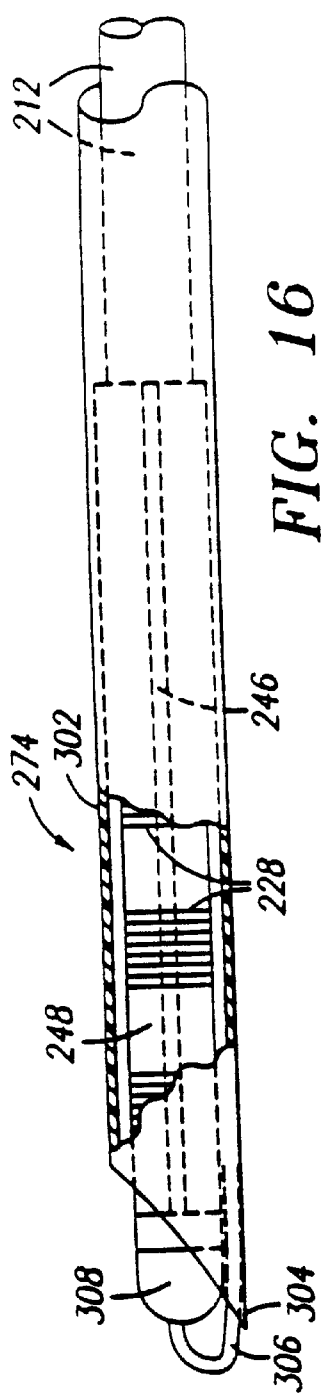
FIG. 16 is a side view of an exemplary multiple electrode loop structure suitable for use with the system shown in FIG. 15, with the loop structure withdrawn within an associated sheath for deployment into a body region.

The structure 274 is carried at the distal end of a catheter tube 212. A sheath 302 is also carried by the catheter tube 212. As FIGS. 16 and 17 show, the distal section 304 of the sheath 302 is joined to the distal end 308 of the structure 274 by a short length of wire 306, e.g., by adhesive or thermal bonding.

The catheter tube 212 is slidable within the sheath 302 to deploy the structure 274. Pushing the catheter tube 212 in the forward direction through the sheath 302 (as shown by arrow 310 in FIG. 17), moves the structure 274 outward from the end of the sheath 302. The wire 306 forms a flexible joint 344, pulling the distal end 308 of the structure 274 toward the sheath 302. The structure 274 thereby is bent into a loop, as FIG. 17 shows. The physician can alter the diameter of the loop structure 274 from large to small, by incrementally moving the catheter tube 312 in the forward direction (arrow 310 in FIG. 17) and rearward direction (arrow 316 in FIG. 17) through the sheath 302. Moving the structure 274 fully in the rearward direction (arrow 316) returns the structure 274 into a low profile, generally straightened configuration within the sheath 302 (as FIG. 16 shows), well suited for introduction into the intended body region.

Figure 18:
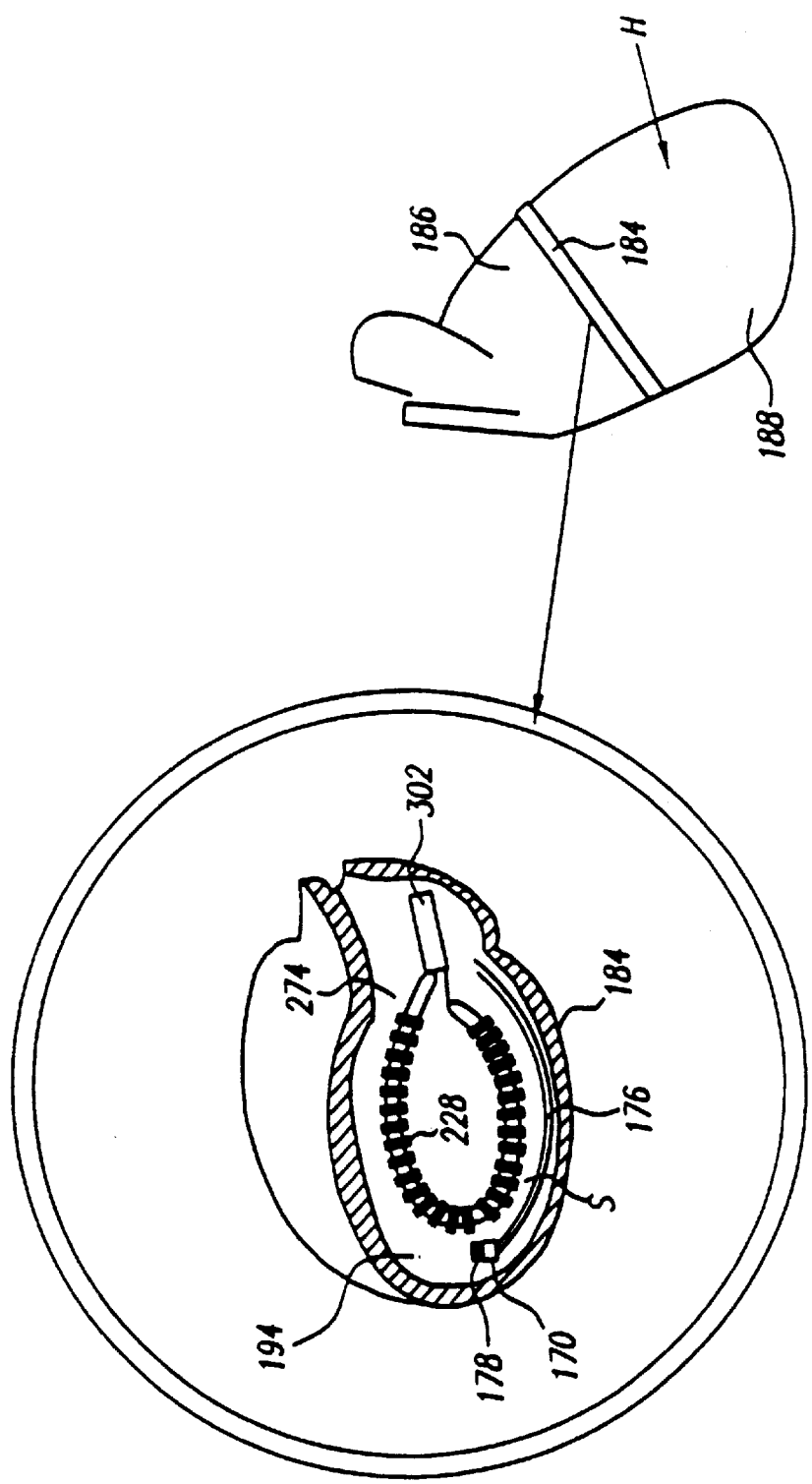
FIG. 18 is a diagrammatic view of the operative element and multiple electrode loop structure shown in FIG. 15 deployed for diagnostic or therapeutic purposes in the annulus region of a human heart.

FIG. 18 shows the operative element 170 and structure 274 deployed in the annulus region 180 of a human heart H. Like FIG. 13, FIG. 18 shows the deployment diagrammatically and is not intended to be anatomically accurate.

In FIG. 18, the loop structure 274 is deployed within an atrium 194 of the heart H. Due to its geometry, the loop structure 274 tends to seek the largest diameter in the atrium 194 and occupy it. The region of largest diameter in an atrium is typically located above and close to the annulus region 184. The loop structure 274 thereby serves to reliably situate itself close to the annulus region 184.

In FIG. 18, the operative element 170 and its electrode 178 are deployed in the space S immediately below (i.e., toward the ventricle 188) of the loop structure 274, which is nearer to the annulus region 184 than the loop structure 274. The physician is able to selectively move the element 170 along the endocardial surface within this space S near the annulus region 184.

As FIG. 15 shows, and functioning in the same manner as previously described, the central processing unit 28 conditions the oscillator 26 to transmit an electrical AC waveform through the electrode 178 carried by the operative element 170. The indifferent electrode 32 comprises the voltage return, coupled to an electrical reference, which, in the illustrated embodiment, is isolated or patient ground 34. The voltage field that is established varies in detected amplitude at each electrode ring 228 on the loop structure 274 according to its distance from the electrode 178 carried by the operative element 170. A proximity-indicating output 198 (designated $P_{(A)}$) is generated for a given electrode ring 228 (where A equals 1 to the number of electrode rings 228 on the loop structure 274), when the prescribed "close condition" between the given ring electrode 228 and the electrode 178 exists.

Figure 19:
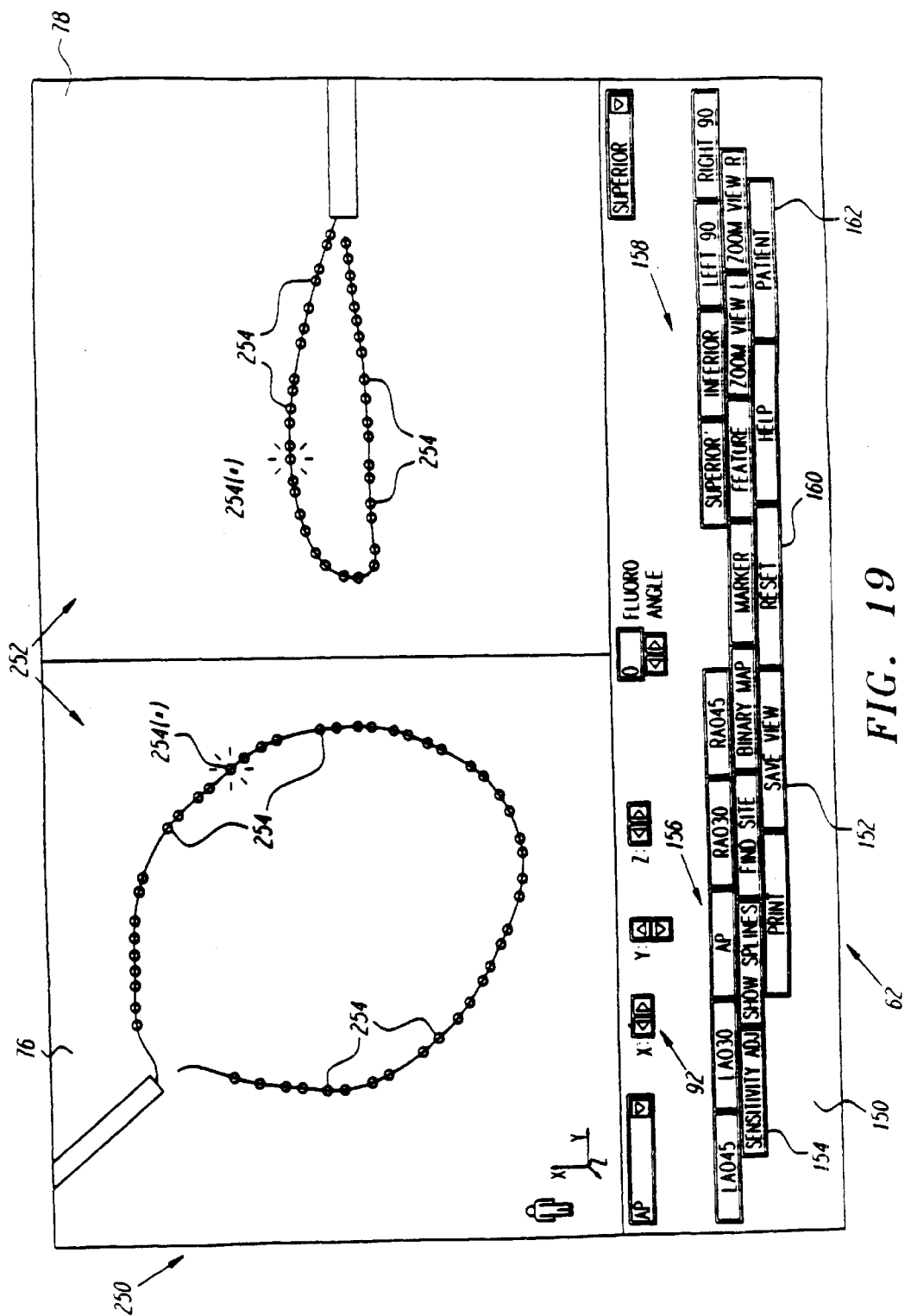
FIG. 19 is a schematic view of an embodiment of a graphical user interface used by the system shown in FIG. 15 to visually display the presence or absence of a proximity-indicated output at each electrode carried by the loop structure.

As previously described in the context of other structures, a graphic display 250 can generate an idealized graphical image 252 (see FIG. 19) for the loop electrode array 274, in which nodes 254 mark the ring electrodes 228. A fluoroscope used in association with the display 250 allows the physician to visualize the actual radius of curvature and orientation of the loop 274 in the atrium. The physician compares the fluoroscopic image and uses the Toolbar 150 (previously described) to manipulate the graphic image 252 to more closely match the view of the fluoroscopic display. The physician can then use the Toolbar 150 to switch views of the graphic image 252 electronically, without manipulating the fluoroscopic display, as previously described.

Using the ring electrodes 228 on the loop structure 274, the physician can pace and sense electrical events in myocardial tissue along the annulus region 184.

Generation of the proximity-indicated output 198 switches "ON" the node 254(*) when the prescribed "close condition" to the roving electrode 178 exits. The display 250 thereby tracks the movement of the roving electrode 178 along the annulus region 184 as mapping and diagnostic functions proceed.

Once mapping identifies a candidate ablation site, the display 250 aids the physician in moving the electrode 178 to the site for the purpose of transmitting ablation energy.

C. Dual Electrode Arrays

Figure 27:
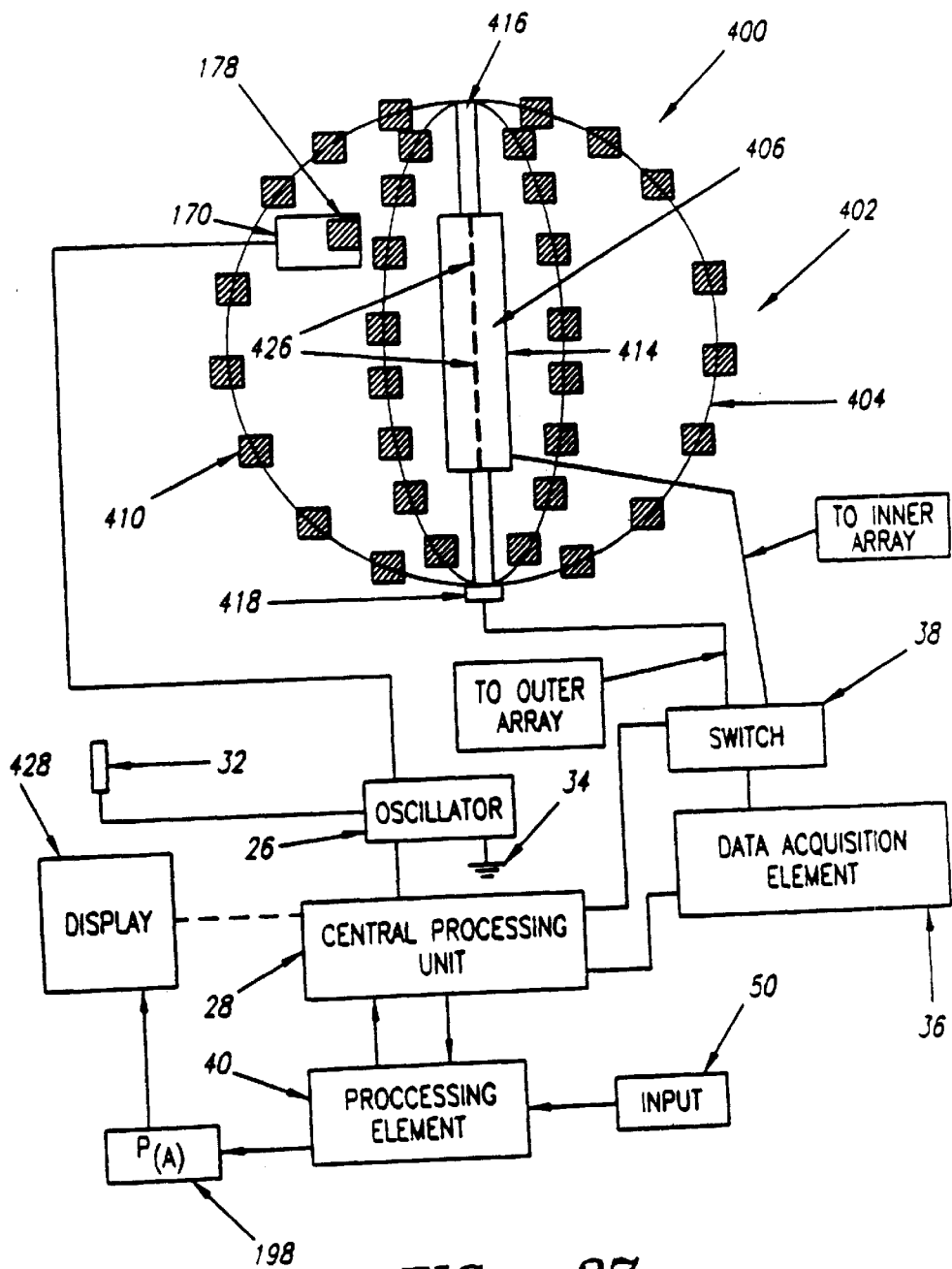
FIG. 27 is schematic view of a system for sensing the position of an operative element within a dual electrode array structure of the type shown in FIGS. 25 and 26.

FIG. 27 shows another embodiment of a position sensing system 400, which locates the position of the same or equivalent operative element 170 and associated electrode 178 shown and described in connection with the preceding embodiments (FIGS. 12 and 15). In this embodiment (see also FIG. 25), the locating probe comprises a three-dimensional structure 402 carrying dual outer and inner arrays of electrodes 404 and 406.

Figure 25:
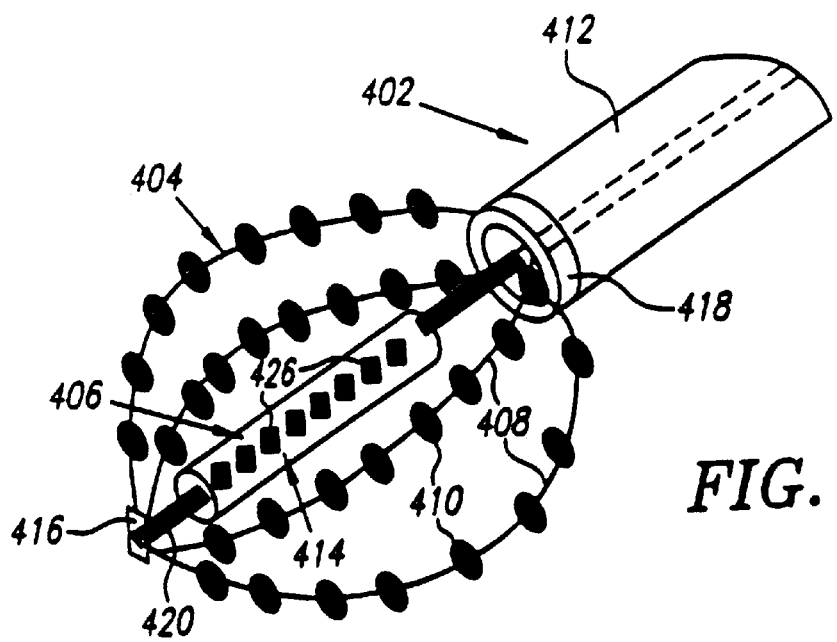
FIG. 25 is an end perspective view of a dual electrode array structure having both an inner array of sensing electrodes and an outer array of sensing electrodes to locate a roving operative element both near a tissue wall and within the middle of an interior body region spaced from the tissue wall.

As best shown in FIG. 25, the outer electrode array 404 comprises an outer structure formed by spaced apart splines elements 408 constrained between a base 418 and a hub 416, in the same manner as the basket structure 14 shown in FIG. 1. Spline elements 408 are carried at the distal end of a catheter tube 412 in the same way that the structure 14 is carried by a catheter tube 45 in FIG. 2A. In FIG. 25, four spline elements 408 are shown for the purpose of illustration.

As in the basket structure 14, each spline element 408 carries a number of electrodes 410. In FIG. 25, each spline element 408 carries eight electrodes 410, for a total of thirty-two electrodes 410 on the outer electrode array 404. Of course, the outer electrode array 404 can comprise a greater or lesser number of spline elements 408 and/or electrodes 410. The hub 416 can also serve as an electrode on the outer array 404.

The inner electrode array 406 shown in FIG. 25 comprises an inner structure 414, formed of electrically insulating material, which is supported by and within the outer electrode array 404. As shown in FIG. 25, the inner structure 414 is retained by a center support wire 420 between the hub 416 and base 418.

In FIG. 25, the inner structure 414 is shown to be a cylindrical tube. However, the inner structure 414 can take other shapes and be constructed differently.

Figure 26:
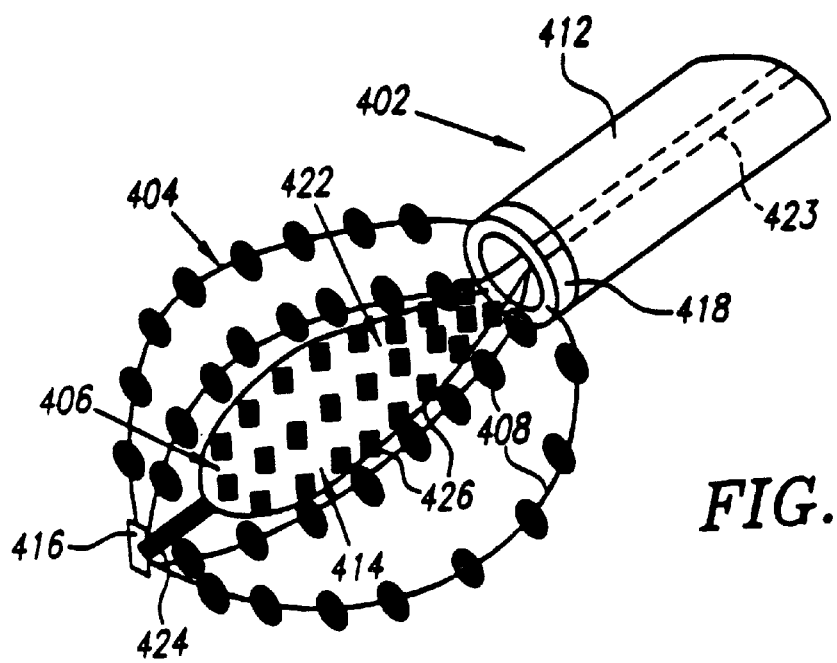
FIG. 26 is an alternative embodiment of a dual electrode array structure having inner and outer arrays of sensing electrodes.

For example, as shown in FIG. 26, the inner structure 414 can comprise an expandable balloon 422. The proximal end of the balloon 422 extends through the base 418 into the interior of the outer electrode array 404. A support wire 424 extends from the distal end of the balloon 422 and is attached to the hub 416. A lumen 423 in the associated catheter tube 412 carries an inflation fluid into the balloon 422, to expand it at time of use. In FIG. 26, when inflated, the balloon 422 has a preformed elliptical shape.

Regardless of its shape or construction, the inner structure 414 carries an array of electrodes 426, position in a spaced-apart pattern on the structure 414. The electrodes 426 can comprise metallic strips of electrically conductive material (e.g., copper alloy, platinum, or stainless steel), attached in the spaced apart pattern on the inner structure 414. Alternatively, the electrodes 426 can be coated on the inner structure 414, using conventional coating techniques or an ion beam assisted deposition (IBAD) process. Preferably, the electrodes 410 on the outer structure 404 and the electrodes 426 on the inner structure 406 are made of substantially equivalent materials.

The number of electrodes 426 carried by the inner structure 414 can vary. Preferably, the number of electrodes 426 on the inner structure 414 should at least equal the number of electrodes 410 on the outer structure 404.

As FIG. 27 shows, the central processing unit 28 conditions the oscillator 26 to transmit an electrical AC waveform through the electrode 178 carried by the operative element 170. The indifferent electrode 32 comprises the voltage return, coupled to an electrical reference, which, in the illustrated embodiment, is isolated or patient ground 34. The voltage field that is established varies in detected amplitude at each electrode 410 or 426 according to its distance from the electrode 178 carried by the operative element 170. The switch 38 serves to couple the data acquisition element 36 to selected electrodes 410 on the outer array 404 or selected electrodes 426 on the inner array 406, or both.

A proximity-indicating output 198 (designated $P_{(A)}$) is generated in the manner previously described for a given electrode 410 or 426, when the prescribed "close condition" between the given electrode 410 or 426 and the electrode 178 exists.

The electrodes 410 on outer electrode array 404 provide information for localizing the roving operative element 170 when it resides close to the tissue walls of the interior body region, e.g., near the endocardial wall, when the structure 402 is deployed in a heart chamber. The electrodes 426 on the inner electrode array 406 provide information for localizing the roving operative element 170 when it resides close to the central region of the interior body region, e.g., inside a heart chamber away from the endocardial wall. Voltage amplitude sensing can be accomplished in sequence by groups of electrodes 410 on the outer array 404, groups of electrodes 426 on the inner array 406, or by groups of electrodes distributed on both the inner and outer arrays 404 and 406.

Figure 28:
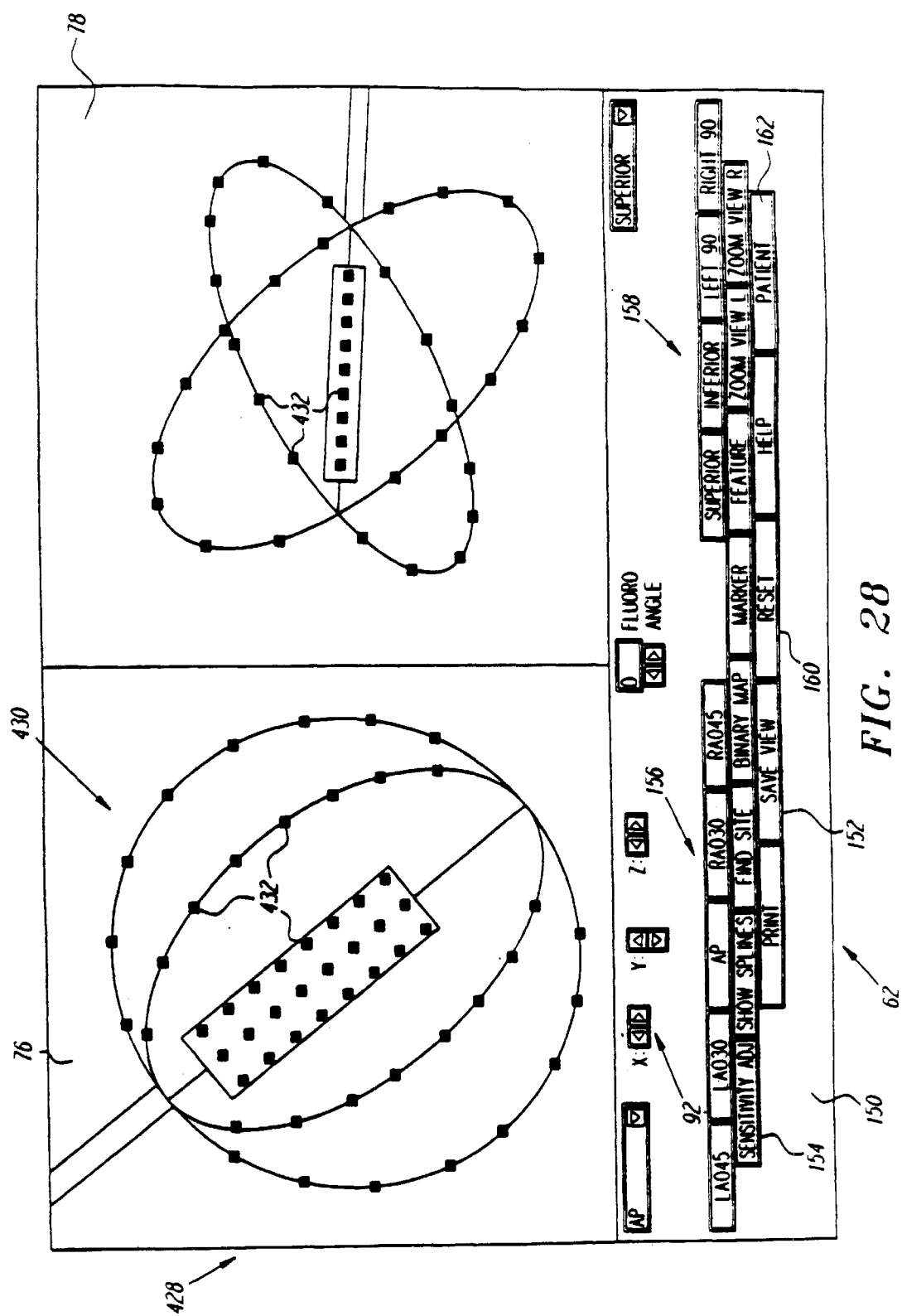
FIG. 28 is a schematic view of an embodiment of a graphical user interface used by the system shown in FIG. 27 to visually display the presence or absence of a proximity-indicated output at each electrode carried by the dual electrode array structure.

As FIG. 28 shows, a graphic display 428 can generate an idealized graphical image 430 for the dual electrode array structure 402, in which nodes 432 mark the electrodes 410 and 426.

Using the electrodes 410 on the outer array 404, the physician can pace and sense electrical events in myocardial tissue. Generation of the proximity-indicated output 198 (as previously described with reference to the basket structure 14) switches "ON" the node 434 when the prescribed "close condition" to the roving electrode 178 exits. Coupled to the dual array sensing structure 402, the display 428 tracks the movement of the roving electrode 178 both near to and far from tissue as diagnostic and therapeutic functions proceed.

Once mapping identifies a candidate ablation site, the display 428 aids the physician in moving the electrode 178 to the site for the purpose of transmitting ablation energy.

The dual array structure 402 can be used in association with the elongated electrode structure 174 or the loop structure 274, previously described. Use of the dual array structure 402 can provide improved navigational accuracy, particularly in interior body regions, away from the tissue wall.

All the previously described features of the GUI 62 can be employed in association with the graphical images 202, 250, or 430. The interpolation function 88 can be used to interpolate multiple proximity-indicated output 198 in the manner shown in FIGS. 8 and 24. Identification codes 94 can be used in the manners shown in FIG. 9 to uniquely identify the particular geometries and physical characteristics of the elongated structure 174, the loop structure 274, the multiple array structure 402, or an other structure deployed. The codes 94 can be employed to create the idealized image 202 or 250 or 430, which can be further manipulated by input from the physician, in the same manner as previously described. Markers 122 and comment windows 124 can be generated in the image 202 or 250 or 430, in the same manner as previously described in connection with FIGS. 10A and 10B. The graphical image 202 or 250 or 430, with associated markers 122 and comment windows 124, can be periodically saved during mapping, and again saved at the instant of ablation, and retained in the patient-specific data base 128, as previously described.

Use of the elongated electrode structure 174, the loop structure 274, and the dual array structure 402 has been described, during which the electrical field is transmitted by the electrode 178 on the operative element 170 to the indifferent electrode 32, and the electrical field is sensed by electrodes carried on the structure 174, 274, or 402. However, it should be appreciated that, as in the embodiment shown in FIGS. 20 to 24, the electrical field can be transmitted by one or more electrodes on the structure 174, or 274, or 402 (simultaneously or in sequence) to the indifferent electrode 32, for sensing by the electrode 178 on the operative element 170. The operative element can also carry multiple sensing electrodes 178 to provide orientation information as well as proximity information, as previously described in connection with FIGS. 22 and 23.

Furthermore, with respect to the dual array structure 402, the electrical field can be transmitted to the indifferent electrode 32 by groups of electrodes on the outer array 404, or groups of electrodes on the inner array 406, or groups of electrodes distributed on both the outer and inner arrays 404 and 406. In this arrangement, the roving electrode 178 (or electrodes, if present) on the operative element 170 can be used to sense the voltage amplitude.

The foregoing GUI and implementing control programs can be implemented using the MS WINDOWS™ application and the standard controls provided by the WINDOWS™ Development Kit, along with conventional graphics software disclosed in public literature.

Various features of the invention are set forth in the following claims.

We claim:

1. A system, comprising:
   an electrode structure adapted to be deployed in a body;
   a roving element adapted to be deployed in the body;
   an operative element carried on one of the electrode structure or roving element;
   a device coupled to the operative element to condition the operative element to perform a diagnostic or therapeutic procedure while deployed in the body; and
   an image controller configured to generate an image of the electrode structure while the operative element performs the procedure, the image depicting a proximity image of the roving element to the electrode structure.

2. A system according to claim 1, wherein the electrode structure comprises an elongated body.

3. A system according to claim 1, wherein the electrode structure comprises a loop.

4. A system according to claim 1, wherein the electrode structure comprises a three-dimensional basket.

5. A system according to claim 1, wherein the electrode structure comprises an outer electrode element and an inner array of electrode elements located within the outer electrode element.

6. A system according to claim 1, wherein the operative element is located on the roving element.

7. A system according to claim 1, wherein the operative element is located on the electrode structure.

8. A system according to claim 1, wherein the image comprises an idealized graphical image.

9. A system according to claim 1, wherein the image controller includes an input for establishing a proximity threshold for the proximity image.

10. A system according to claim 1, the image controller comprising an output coupled to a display device for visually presenting the image.

11. A method of recording the use of structures deployed inside a body, comprising:

introducing in a body an electrode structure having one or more electrodes;

transmitting electrical energy to one or more of the electrodes to create an electrical field between the electrode or electrodes and a reference electrode;

introducing in the body a roving element having one or more electrodes, one of the electrode structure and roving element carrying an operative element conditioned to perform a diagnostic or therapeutic procedure; and generating an image of the proximity of the roving element to the electrode structure while the operative element performs the procedure.

12. A method according to claim 11, wherein generating the image of the proximity of the roving element to the electrode structure is based in part on voltage amplitudes sensed by one or more of the electrodes in the electrical field.

13. A method according to claim 12, wherein generating an image includes inputting a threshold proximity value for comparison to sensed voltage amplitudes.

14. A method according to claim 11, wherein generating an image includes displaying the output.

* * * * *